US009950066B2

(12) United States Patent
Krause et al.

(10) Patent No.: US 9,950,066 B2
(45) Date of Patent: *Apr. 24, 2018

(54) FORMULATION OF HUMAN ANTIBODIES FOR TREATING TNF-ALPHA ASSOCIATED DISORDERS

(71) Applicant: AbbVie Biotechnology Ltd, Hamilton (BM)

(72) Inventors: Hans-Juergen Krause, Gruenstadt (DE); Lisa Baust, Ludwigshafen (DE); Michael Dickes, Rodersheim-Gronau (DE)

(73) Assignee: AbbVie Biotechnology Ltd, Hamilton (BM)

(*) Notice: Subject to any disclaimer, the term of this patent is extended or adjusted under 35 U.S.C. 154(b) by 0 days.

This patent is subject to a terminal disclaimer.

(21) Appl. No.: 15/095,393

(22) Filed: Apr. 11, 2016

(65) Prior Publication Data

US 2017/0056498 A1     Mar. 2, 2017

Related U.S. Application Data

(63) Continuation of application No. 14/826,357, filed on Aug. 14, 2015, now Pat. No. 9,327,032, which is a continuation of application No. 14/558,182, filed on Dec. 2, 2014, now Pat. No. 9,114,166, which is a continuation of application No. 14/453,490, filed on Aug. 6, 2014, now Pat. No. 8,916,158, which is a continuation of application No. 14/322,581, filed on Jul. 2, 2014, now Pat. No. 8,911,741, which is a continuation of application No. 14/091,938, filed on Nov. 27, 2013, now Pat. No. 8,795,670, which is a continuation of application No. 13/471,820, filed on May 15, 2012, now Pat. No. 8,932,591, which is a continuation of application No. 10/525,292, filed as application No. PCT/IB03/04502 on Aug. 15, 2003, now Pat. No. 8,216,583, which is a continuation of application No. 10/222,140, filed on Aug. 16, 2002, now abandoned.

(51) Int. Cl.
| | |
|---|---|
| A61K 39/395 | (2006.01) |
| C07K 16/00 | (2006.01) |
| C07K 16/22 | (2006.01) |
| A61K 9/19 | (2006.01) |
| C07K 16/24 | (2006.01) |
| A61K 9/00 | (2006.01) |
| A61K 47/10 | (2017.01) |
| A61K 47/12 | (2006.01) |
| A61K 47/22 | (2006.01) |
| A61K 47/18 | (2017.01) |
| A61K 47/26 | (2006.01) |
| A61K 47/02 | (2006.01) |
| C07K 14/525 | (2006.01) |
| A61K 39/00 | (2006.01) |

(52) U.S. Cl.
CPC ...... *A61K 39/39591* (2013.01); *A61K 9/0019* (2013.01); *A61K 9/19* (2013.01); *A61K 39/3955* (2013.01); *A61K 47/02* (2013.01); *A61K 47/10* (2013.01); *A61K 47/12* (2013.01); *A61K 47/183* (2013.01); *A61K 47/22* (2013.01); *A61K 47/26* (2013.01); *C07K 16/241* (2013.01); *A61K 2039/505* (2013.01); *C07K 2317/21* (2013.01); *C07K 2317/76* (2013.01); *C07K 2317/92* (2013.01); *C07K 2317/94* (2013.01)

(58) Field of Classification Search
CPC .. C07K 16/241; C07K 16/24; C07K 2316/96; C07K 2317/21; C07K 2317/76; C07K 2317/94; A61K 39/39591; A61K 39/3955; A61K 2039/505; A61K 39/39533; A61K 39/395

See application file for complete search history.

(56) References Cited

U.S. PATENT DOCUMENTS

| | | | |
|---|---|---|---|
| 4,091,089 A | 5/1978 | Chichibu | |
| 4,396,608 A | 8/1983 | Tenold | |
| 4,597,966 A | 7/1986 | Zolton et al. | |
| 4,877,608 A | 10/1989 | Lee | |
| 4,897,465 A | 1/1990 | Cordle et al. | |
| 5,096,885 A | 3/1992 | Pearlman | |
| 5,231,024 A | 7/1993 | Moeller et al. | |
| 5,237,054 A | 8/1993 | Brinks et al. | |
| 5,358,708 A | 10/1994 | Patel et al. | |
| 5,608,038 A | 3/1997 | Eibl et al. | |
| 5,654,403 A | 8/1997 | Smith et al. | |
| 5,656,730 A | 8/1997 | Lee | |
| 5,792,838 A | 8/1998 | Smith et al. | |
| 5,917,021 A | 6/1999 | Lee | |
| 5,945,098 A | 8/1999 | Sarno et al. | |
| 5,981,485 A | 11/1999 | O'Connor | |
| 5,998,378 A | 12/1999 | Kriegler et al. | |
| 6,015,557 A | 1/2000 | Tobinick et al. | |
| 6,024,938 A | 2/2000 | Corbo et al. | |
| 6,090,382 A | 7/2000 | Salfeld et al. | |
| 6,165,467 A | 12/2000 | Hagiwara et al. | |
| 6,171,586 B1 | 1/2001 | Lam et al. | |
| 6,177,077 B1 | 1/2001 | Tobinick | |
| 6,235,281 B1 | 5/2001 | Stenzel et al. | |
| 6,238,664 B1 | 5/2001 | Hellerbrand et al. | |
| 6,252,055 B1 | 6/2001 | Relton | |

(Continued)

FOREIGN PATENT DOCUMENTS

| | | |
|---|---|---|
| CA | 1329760 | 5/1994 |
| CA | 2241319 | 1/1997 |

(Continued)

OTHER PUBLICATIONS

2015 Express Scripts Basic Formulary (Aug. 2014) (2 pages).

(Continued)

*Primary Examiner* — Bridget E Bunner
(74) *Attorney, Agent, or Firm* — Haley Guiliano LLP; James F. Haley, Jr.; Brian M. Gummow

(57) ABSTRACT

A liquid aqueous pharmaceutical formulation is described which has a high protein concentration, a pH of between about 4 and about 8, and enhanced stability.

20 Claims, No Drawings

(56) References Cited

U.S. PATENT DOCUMENTS

| | | |
|---|---|---|
| 6,258,562 B1 | 7/2001 | Salfeld et al. |
| 6,267,958 B1 | 7/2001 | Andya et al. |
| 6,281,336 B1 | 8/2001 | Laursen et al. |
| 6,379,666 B1 | 4/2002 | Tobinick |
| 6,419,934 B1 | 7/2002 | Tobinick |
| 6,419,944 B2 | 7/2002 | Tobinick |
| 6,423,321 B2 | 7/2002 | Tobinick |
| 6,428,787 B1 | 8/2002 | Tobinick |
| 6,485,725 B1 | 11/2002 | Hirao et al. |
| 6,485,932 B1 | 11/2002 | McInosh et al. |
| 6,509,015 B1 | 1/2003 | Salfeld et al. |
| 6,627,439 B2 | 9/2003 | Hoevel |
| 6,737,405 B2 | 5/2004 | Roemisch et al. |
| 6,818,613 B2 | 11/2004 | Sharma et al. |
| 6,835,823 B2 | 12/2004 | Le |
| 6,850,177 B2 | 2/2005 | Donovan et al. |
| 6,875,432 B2 | 4/2005 | Liu et al. |
| 6,875,848 B2 | 4/2005 | Debart |
| 6,902,734 B2 | 6/2005 | Giles-Komar |
| 7,070,775 B2 | 7/2006 | Le et al. |
| 7,141,542 B2 | 11/2006 | Cowan et al. |
| 7,220,409 B2 | 5/2007 | Norman et al. |
| 7,223,394 B2 | 5/2007 | Salfeld et al. |
| 7,250,165 B2 | 7/2007 | Heavner et al. |
| 7,276,239 B2 | 10/2007 | Le et al. |
| 7,318,931 B2 | 1/2008 | Okumu et al. |
| 7,495,018 B2 | 2/2009 | Ohkawa |
| 7,541,031 B2 | 6/2009 | Salfeld et al. |
| 7,588,761 B2 | 9/2009 | Salfeld et al. |
| 7,592,004 B2 | 9/2009 | Kaisheva |
| 7,648,702 B2 | 1/2010 | Gombotz |
| 7,740,842 B2 | 6/2010 | Arvinte |
| 7,820,651 B2 | 10/2010 | Herdeis et al. |
| 7,863,426 B2 | 1/2011 | Wan et al. |
| 7,906,119 B1 | 3/2011 | Rosen |
| 7,919,264 B2 | 4/2011 | Maksymowych et al. |
| 8,216,583 B2 * | 7/2012 | Kruase ............... A61K 9/19 424/130.1 |
| 8,465,739 B2 | 6/2013 | Kaisheva |
| 8,632,778 B2 | 1/2014 | Kakuta |
| 8,795,670 B2 * | 8/2014 | Krause ............... A61K 9/19 424/130.1 |
| 8,802,100 B2 * | 8/2014 | Krause ............... A61K 9/19 424/130.1 |
| 8,802,101 B2 * | 8/2014 | Krause ............... A61K 9/19 424/130.1 |
| 8,802,102 B2 * | 8/2014 | Krause ............... A61K 9/19 424/130.1 |
| 8,911,741 B2 * | 12/2014 | Krause ............... A61K 9/19 424/130.1 |
| 8,916,157 B2 * | 12/2014 | Krause ............... A61K 9/19 424/130.1 |
| 8,916,158 B2 * | 12/2014 | Krause ............... A61K 9/19 424/130.1 |
| 8,932,591 B2 * | 1/2015 | Krause ............... A61K 9/19 424/130.1 |
| 8,940,305 B2 * | 1/2015 | Krause ............... A61K 9/19 424/130.1 |
| 9,114,166 B2 * | 8/2015 | Krause ............... A61K 9/19 |
| 9,220,781 B2 * | 12/2015 | Krause ............... A61K 9/19 |
| 9,272,041 B2 * | 3/2016 | Krause ............... A61K 9/19 |
| 9,272,042 B2 * | 3/2016 | Krause ............... A61K 9/19 |
| 9,289,497 B2 * | 3/2016 | Krause ............... A61K 9/19 |
| 9,295,725 B2 * | 3/2016 | Krause ............... A61K 9/19 |
| 9,302,011 B2 * | 4/2016 | Krause ............... A61K 9/19 |
| 9,327,032 B2 * | 5/2016 | Krause ............... A61K 9/19 |
| 2001/0004456 A1 | 6/2001 | Tobinick |
| 2001/0016195 A1 | 8/2001 | Tobinick |
| 2001/0026801 A1 | 10/2001 | Tobinick |
| 2003/0012786 A1 | 1/2003 | Teoh et al. |
| 2003/0049725 A1 | 3/2003 | Heavner et al. |
| 2003/0124119 A1 | 7/2003 | Yamazaki |
| 2003/0138417 A1 | 7/2003 | Kaisheva et al. |
| 2003/0161828 A1 | 8/2003 | Abdelghany et al. |
| 2003/0180287 A1 | 9/2003 | Gombotz et al. |
| 2003/0190316 A1 | 10/2003 | Kakuta et al. |
| 2003/0206898 A1 | 11/2003 | Fischkoff et al. |
| 2003/0219438 A1 | 11/2003 | Salfeld et al. |
| 2003/0235585 A1 | 12/2003 | Fischkoff et al. |
| 2004/0009172 A1 | 1/2004 | Fischkoff et al. |
| 2004/0033228 A1 | 2/2004 | Krause et al. |
| 2004/0038878 A1 | 2/2004 | Tanikawa et al. |
| 2004/0126372 A1 | 7/2004 | Banerjee et al. |
| 2004/0126373 A1 | 7/2004 | Banerjee et al. |
| 2004/0131614 A1 | 7/2004 | Banerjee et al. |
| 2004/0136989 A1 | 7/2004 | Banerjee et al. |
| 2004/0136990 A1 | 7/2004 | Banerjee et al. |
| 2004/0136991 A1 | 7/2004 | Banerjee et al. |
| 2004/0151722 A1 | 8/2004 | Banerjee et al. |
| 2004/0156835 A1 | 8/2004 | Imoto et al. |
| 2004/0166111 A1 | 8/2004 | Kaymakcalan et al. |
| 2004/0170623 A1 | 9/2004 | Arvinte et al. |
| 2004/0219142 A1 | 11/2004 | Banerjee et al. |
| 2004/0221378 A1 | 11/2004 | Conway |
| 2005/0118163 A1 | 6/2005 | Mizushima et al. |
| 2005/0118167 A1 | 6/2005 | Okada |
| 2005/0214278 A1 | 9/2005 | Kakuta et al. |
| 2006/0009385 A1 | 1/2006 | Hoffman et al. |
| 2006/0083741 A1 | 4/2006 | Hoffman et al. |
| 2006/0127395 A1 | 6/2006 | Arvinte et al. |
| 2006/0153846 A1 | 7/2006 | Krause et al. |
| 2006/0182740 A1 | 8/2006 | Yang et al. |
| 2006/0246073 A1 | 11/2006 | Knight et al. |
| 2007/0041905 A1 | 2/2007 | Hoffman et al. |
| 2007/0053906 A1 | 3/2007 | Samaritani et al. |
| 2007/0071747 A1 | 3/2007 | Hoffman et al. |
| 2007/0081996 A1 | 4/2007 | Hoffman et al. |
| 2007/0172897 A1 | 7/2007 | Maksymowych et al. |
| 2007/0202104 A1 | 8/2007 | Banerjee et al. |
| 2007/0243185 A1 | 10/2007 | Gombotz et al. |
| 2007/0292442 A1 | 12/2007 | Wan et al. |
| 2008/0118496 A1 | 5/2008 | Medich et al. |
| 2008/0131374 A1 | 6/2008 | Medich et al. |
| 2008/0166348 A1 | 7/2008 | Kupper et al. |
| 2008/0193466 A1 | 8/2008 | Banergee et al. |
| 2008/0227136 A1 | 9/2008 | Pia et al. |
| 2008/0286280 A1 | 11/2008 | Kallmeyer et al. |
| 2008/0311043 A1 | 12/2008 | Hoffman et al. |
| 2009/0017472 A1 | 1/2009 | Stuhlmuller et al. |
| 2009/0028794 A1 | 1/2009 | Medich et al. |
| 2009/0110679 A1 | 4/2009 | Li et al. |
| 2009/0123378 A1 | 5/2009 | Wong et al. |
| 2009/0148513 A1 | 6/2009 | Fraunhofer et al. |
| 2009/0155205 A1 | 6/2009 | Salfeld et al. |
| 2009/0226530 A1 | 9/2009 | Lassner et al. |
| 2009/0239259 A1 | 9/2009 | Hsieh et al. |
| 2009/0258018 A1 | 10/2009 | Medich et al. |
| 2009/0271164 A1 | 10/2009 | Peng et al. |
| 2009/0280065 A1 | 11/2009 | William et al. |
| 2009/0291062 A1 | 11/2009 | Fraunhofer et al. |
| 2009/0304682 A1 | 12/2009 | Hoffman et al. |
| 2009/0317399 A1 | 12/2009 | Pollack et al. |
| 2010/0003243 A1 | 1/2010 | Okun et al. |
| 2010/0016557 A1 | 1/2010 | Salfeld et al. |
| 2010/0021451 A1 | 1/2010 | Wong et al. |
| 2010/0034823 A1 | 2/2010 | Borhani et al. |
| 2010/0040630 A1 | 2/2010 | Elden et al. |
| 2010/0160894 A1 | 6/2010 | Julian et al. |
| 2010/0278822 A1 | 11/2010 | Fraunhofer et al. |
| 2011/0002935 A1 | 1/2011 | Wan et al. |
| 2011/0054414 A1 | 3/2011 | Shang et al. |
| 2011/0171227 A1 | 7/2011 | Okun et al. |
| 2012/0263731 A1 | 10/2012 | Fraunhofer et al. |
| 2013/0156760 A1 | 6/2013 | Fraunhofer et al. |

FOREIGN PATENT DOCUMENTS

| | | |
|---|---|---|
| EP | 0186833 | 7/1986 |
| EP | 0218868 | 4/1987 |
| EP | 0230574 | 8/1987 |
| EP | 0374510 | 6/1990 |
| EP | 0419251 | 3/1991 |

(56) References Cited

FOREIGN PATENT DOCUMENTS

| | | |
|---|---|---|
| EP | 0453898 | 10/1991 |
| EP | 0486526 | 5/1992 |
| EP | 0417191 | 10/1993 |
| EP | 0585705 | 3/1994 |
| EP | 0614984 | 9/1994 |
| EP | 0531539 | 6/1998 |
| EP | 1174148 | 1/2002 |
| EP | 1254666 | 11/2002 |
| EP | 1575597 | 9/2005 |
| EP | 1737450 | 1/2007 |
| EP | 1324776 | 7/2009 |
| EP | 1528933 | 5/2012 |
| WO | WO-1986000530 | 1/1986 |
| WO | WO-1989011298 | 11/1989 |
| WO | WO-1990001191 | 2/1990 |
| WO | WO-1990011091 | 10/1990 |
| WO | WO-1991004054 | 4/1991 |
| WO | WO-1992003145 | 3/1992 |
| WO | WO-1992011383 | 7/1992 |
| WO | WO-1992016221 | 10/1992 |
| WO | WO-1992016553 | 10/1992 |
| WO | WO-1992017583 | 10/1992 |
| WO | WO-1993008837 | 5/1993 |
| WO | WO-1993011793 | 6/1993 |
| WO | WO-1993019751 | 10/1993 |
| WO | WO-1994008609 | 4/1994 |
| WO | WO-1994020139 | 9/1994 |
| WO | WO-1995003826 | 2/1995 |
| WO | WO-1996007429 | 3/1996 |
| WO | WO-1997004801 | 2/1997 |
| WO | WO-1997006251 | 2/1997 |
| WO | WO-1997029131 | 8/1997 |
| WO | WO-1997045140 | 12/1997 |
| WO | WO-1998004281 | 2/1998 |
| WO | WO-1998022136 | 5/1998 |
| WO | WO-1998044948 | 10/1998 |
| WO | WO-1998056418 | 12/1998 |
| WO | WO-1999037329 | 7/1999 |
| WO | WO-2000012502 | 3/2000 |
| WO | WO-2000050079 | 8/2000 |
| WO | WO-2000056772 | 9/2000 |
| WO | WO-2000067789 | 11/2000 |
| WO | WO-2000067798 | 11/2000 |
| WO | WO-2001000245 | 1/2001 |
| WO | WO-2001043773 | 6/2001 |
| WO | WO-2001047554 | 7/2001 |
| WO | WO-2001049321 | 7/2001 |
| WO | WO-2001060420 | 8/2001 |
| WO | WO-2002012500 | 2/2002 |
| WO | WO-2002012502 | 2/2002 |
| WO | WO-2002030463 | 4/2002 |
| WO | WO-2002064166 | 8/2002 |
| WO | WO-2002072636 | 9/2002 |
| WO | WO-2002096457 | 12/2002 |
| WO | WO-2002100330 | 12/2002 |
| WO | WO-2003009817 | 2/2003 |
| WO | WO-2003039485 | 5/2003 |
| WO | WO-2003066681 | 8/2003 |
| WO | WO-2004007520 | 1/2004 |
| WO | WO-2006138181 | 12/2006 |
| WO | WO-2007024705 | 9/2007 |
| WO | WO-2013164837 | 11/2013 |
| WO | WO-2014039903 | 3/2014 |

OTHER PUBLICATIONS

AbbVie Facts and Arguments in Support of Opposition Against EP1324776 B1, filed Jun. 16, 2010 (19 pages).
Abbvie Opposition filed against EP1528933, on Feb. 26, 2016 (CAS Registry for Adalimumab) (6 pages).
AbbVie's Grounds of Appeal in Opposition of EP1528933, filed Feb. 26, 2016 (27 pages).
Additional Experimental Results for EP03748438 (sic 439) Abbott Biotechnology, submitted May 15, 2009, in Prosecution of EP1528933 (26 pages).
Arakawa, et al., "Protection of bovine serum albumin from aggregation by Tween 80," Journal of Pharmaceutical Sciences, 89(5):646-51 (2000).
Aulton, Pharmaceutics, The Science of Dosage Form Design, Second Edition, Churchill Livingstone, New York, 317-318, 544-553 (2002) (15 pages).
Bischoff, et al., "Deamidation of asparagine and glutamine residues in proteins and peptides: structural determinants and analytical methodology," Journal of Chromatography B, 662(2):261-278 (1994).
Capasso, et al., "Effect of the three-dimensional structure on the deamidation reaction of ribonuclease A," Journal of Peptide Research, 54(5):377-382 (1999).
Capasso, et al., "First Evidence of Spontaneous Deamidation of Glutamine Residue via Cyclic Imide to a- and y-Glutamic Residue under Physiological Conditions," Journal of the Chemical Society, Chemical Communications, 1667-1668 (1991).
CVS/CaremarkTM Performance Drug List (Oct. 2015) (10 pages).
Decision in Opposition Proceedings Revoking EP1528933 B1, Sep. 9, 2015 (46 pages).
Declaration of Brian Reisetter, RPh, MBA, Ph.D., dated May 4, 2016 (15 pages).
Declaration of Mark C. Manning, Ph.D., dated May 6, 2016 (163 pages).
Dobrow, DTC Report : DTC Gets Smart, Medical Marketing & Media (Apr. 1, 2014) (5 pages).
Dobrow, MM&M 2014 Large Pharma Marketing Team of the Year: Humira, Medical Marketing & Media (Jan. 1, 2014) (2 pages).
DrugBank: Adalimumab, www.drugbank.ca/drugs/DB00051, last Visited May 5, 2016 (15 pages).
Enbrel (etanercept), FDA Arthritis Advisory Committee, Aug. 17, 2001, Immunex Corporation and Wyeth-Ayerst Laboratories (55 pages).
Gatlin, et al., "Formulation and Administration Techniques to Minimize Injection Pain and Tissue Damage Associated with Parenteral Products," Injectable Drug Development: Techniques to Reduce Pain and Irritation, pp. 401-425 (1999).
Gennaro, ed., Remington: The Science and Practice of Pharmacy, 20th ed., Solutes, 785-786 (2000) (10 pages).
Gilbert, et al., "SC versus IV delivery: Reducing costs while increasing patient satisfaction," Hematology & Oncology News & Issues, 4(12):25-29 (2005).
Goolcharran, et al., "The effects of a histidine residue on the C-terminal side of an asparaginyl residue on the rate of deamidation using model pentapeptides," Journal of Pharmaceutical Sciences, 89(6):818-825 (2000).
Hendrickson, "Birth of a Blockbuster: Abbott Mounts Humira's Marketing Campaign," Boston Business Journal Article (Oct. 20, 2003), Last Accessed Mar. 25, 2016 (4 pages).
Humira® Label, Nov. 2015 (90 pages).
Jorgensen, et al., "Pain assessment of subcutaneous injections," Annals of Pharmacotherapy, 30(7-8):729-732 (1996).
Keystone, et al., "The Fully Human Anti-TNF Monoclonal Antibody, Adalimumab (D2E7), Dose Ranging Study: The 24-Week Clinical Results in Patients with Active RA on Methotrexate Therapy (The Armada Trial)," Annual European Congress of Rheumatology, Abstract OP0086 (Jun. 13-16, 2001) (1 page).
Langer, et al., "The art of entrepreneurship," Science, 346(6213):1146 (2014) (2 pages).
McDonnell, "Production of Antibodies in Hybridoma and Nonhybridoma Cell Lines," Chapter 3, Animal Cell Culture, Cell Engineering, 9:65-88(ed. M. Al-Rubeai, 2015) (24 pages).
Miller, "Abbott Ramps Up Biotech Manufacturing to Meet Humira Demand," Pharmaceutical Technology (Mar. 2003) (4 pages).
Nabuchi, et al., "The stability and degradation pathway of recombinant human parathyroid hormone: deamidation of asparaginyl residue and peptide bond cleavage at aspartyl and asparaginyl residues," Pharmaceutical Research, 14(12):1685-1690 (1997).

(56) References Cited

OTHER PUBLICATIONS

Paborji, et al., "Chemical and physical stability of chimeric L6, a mouse-human monoclonal antibody," Pharmaceutical Research, 11(5):764-771 (1994).
Patel, et al., "Chemical pathways of peptide degradation. II. Kinetics of deamidation of an asparaginyl residue in a model hexapeptidee," Pharmaceutical Research, 7(7):703-711 (1990).
Patent Term Extension Certification Salfeld U.S. Pat. No. 6,090,382, stamped Apr. 12, 2007 (1 page).
Patent Term Extension Salfeld U.S. Pat. No. 6,090,032 (1 page) (undated).
Perkins, et al., "Determination of the Origin of Charge Heterogeneity in a Murine Monoclonal Antibody," Pharmaceutical Research, 17(9):1110-1117 (2000).
Petition for Inter Partes Review, *Coherus BioSciences Inc.* v. *AbbVie Biotechnology Ltd.*, U.S. Pat. No. 9,114,166, May 9, 2016 (77 pages).
Physicians' Desk Reference, 56th ed., pp. 582-592, 988-991, 1434-1437, 1752-1760, 1772-1774, 1930-1934, 2502-2507, 3140-3142, (2002), received Nov. 28, 2001 (47 pages).
Physicians' Desk Reference, 56th ed., pp. 914-915, 917-919, 925-931, 992-995, 1178-1182, 1414-1417, 1428-1430, 1752-1755, 1958-1962, 2028-2029, 2295-2297, 2498-2052, 3046-3047 (2002), received Nov. 28, 2001 (50 pages).
Physicians' Desk Reference, 56th ed., Suppl. A, pp. A4-A9, (2002), received Sep. 11, 2002 (8 pages).
Physicians' Desk Reference, 57th ed., Suppl. A, pp. A64-A67, A84-A88, (2003), received Aug. 1, 2003 (11 pages).
PowerPoint by AbbVie CEO Richard Gonzalez, "AbbVie Long-Term Strategy," Oct. 30, 2015 (33 pages).
Preliminary Ruling in Opposition Proceedings Revoking EP1528933 B1, Oct. 22, 2014 (12 pages).
Rau, et al., Long-Term Efficacy and Tolerability of Multiple I.V. Doses of the Fully Human Anti-TNF-Antibody D2E7 in Patients with Rheumatoid Arthritis, Arthritis Rheum., 41(9), S55 (Sep. 1998).
Schattenkirchner, et al., "Efficacy and Tolerability of Weekly Subcutaneous Injections of the Fully Human Anti-TNF Antibody D2E7 in Patients with Rheumatoid Arthritis—Results of a Phase I Study," Arthritis and Rheumatism, 41(9):557 (Sep. 1998) (3 pages).
Scotchler, et al., "Deamidation of glutaminyl residues: dependence on pH, temperature, and ionic strength," Analytical Biochemistry, 59(1):319-322 (1974)
Sorbera, et al., "Adalimumab," Drugs of the Future, 26(7):639-646 (2001).
The Official Comopendia of Standards, United States Pharmacopeia and National Formulary (USP 24-NF 19), vol. 2. Rockville, MD: United States Pharmacopeia Convention; 1999: 1971-1977,2011-2021,2404-2406 (24 pages).
United Healthcare 2015 Four-Tier Prescription Drug List (Jul. 1, 2015) (35 pages).
van de Putte, et al., "A Single Dose Placebo Controlled Phase I Study of the Fully Human Anti-TNF Antibody D2E7 in Patients with Rheumatoid Arthritis," Arthritis and Rheumatism, 41(9):557 (Sep. 1998) (4 pages).
van de Putte, et al., "Efficacy of the Fully Human Anti-TNF Antibody D2E7 in Rheumatoid Arthritis," Arthritis and Rheumatism, 42(9):S400 (Sep. 1999) (3 pages).
van de Putte, et al., "Six Month Efficacy of the Fully Human AntiTNF Antibody D2E7 in Rheumatoid Arthritis," Annals of the Rheumatic Diseases, 59(1):Op.056 (2000) (2 pages).
Weaver, "Abbott Drug Unit Embarks on New Life Without Parent," The Wall Street Journal (Jan. 2, 2013) (3 pages).
Wright, "Nonenzymatic deamidation of asparaginyl and glutaminyl residues in proteins," Critical Reviews in Biochemistry and Molecular Biology, 26(1):1-52 (1991).
Zhang, et al., "Comparative Study on Kinetics of Nonenzymatic Deamidation of Soy Protein and Egg White Lysozyme," Journal of Agricultural and Food Chemistry, 41(12):2286-2290 (1993).

"Campath®", Physicians' Desk Reference, 992-995, 56th ed. (2002) (6 pages).
"Nutropin AQ®", Physicians' Desk Reference, 1420-1423, 56th ed. (2002) (6 pages).
"Orthoclone OKT®3 Sterile Solution," Physicians' Desk Reference, 2498-2502, 56th ed. (2002) (7 pages).
"Reopro®", Physicians' Desk Reference, 1958-1962, 56th ed. (2002) (7 pages).
"Rituxan®", Physicians' Desk Reference, 1428-1430, 1750-1752, 56th ed. (2002) (8 pages).
"Winrho SDF™", Physicians' Desk Reference, 2297-2299, 56th ed. (2002) (5 pages).
Abbott Laboratories 2003 Annual Report, Abbott Laboratories (2004) (80 pages).
Activase (alteplase) [package insert]. South San Francisco, CA: Genentech, Inc. (2002) (32 pages).
Adalimumab entry from National Library of Medicine website: www. nlm.nih.gov/cgi/mesh; printed on Sep. 28, 2009.
Akers et al., "Development and Manufacture of Protein Pharmaceuticals (Pharmaceutical Biotechnology)", Chapter 2: "Formulation Development of Protein Dosage Forms", Kluver Academic/Plenum, pub., New York, vol. 14: 47-127 (2002).
Antoni et al., "Side effects of anti-TNF therapy: Current knowledge," Clinical and Experimental Rheumatology, 20(suppl. 28):S-152-S-157 (2002).
Arakawa et al., "Protein-Solvent Interactions in Pharmaceutical Formulations", Pharmaceutical Research 8(3):285-291 (1991).
Aranesp (dargbepoetin alpha) [package insert]. Thousand Oaks, CA: Amgen Inc. (2002) (22 pages).
Arend et al., "Inhibition of the production and effects of interleukin-1 and tumor necrosis factor alpha in rheumatoid arthritis," Arthritis & Rheumatism, 38(2):151-160 (1995).
Bam et al., "Tween Protects Recombinant Human Growth Hormone against Agitation-Induced Damage via Hydrophobic Interactions", Journal of Pharmaceutical Science, 87(12):1554-1559 (1998).
Banks, et al., "Native-State Solubility and Transfer Free Energy as Predictive Tools for Selecting Excipients to Include in Protein Formulation Development Studies," Journal of Pharmaceutical Sciences, 101(8):2720-2732 (2012).
Barrera et al., "Effects of treatment with a fully human antitumour necrosis factor alpha monoclonal antibody on the local and systemic homeostasis of interleukin 1 and TNF alpha in I patients with rheumatoid arthritis," Annals of the Rheumatic Diseases, 60(7):660-669 (2001).
Bendtzen et al., "Auto-Antibodies to IL-1α and TNFα in Normal Individuals and in Infectious and Immunoinflammatory Disorders," The Physiological and Pathological Effects of Cytokines, 10B:447-452 (1990).
Bertolini et al., "Stimulation of bone resorption and inhibition of bone formation in vitro by human tumour necrosis factors," Nature, 319(6053):516-518 (1986).
Beutler et al., "The biology of cachectin/TNF—a primary mediator of the host response," Annual Review of Immunology, 7:625-655 (1989).
Beutler et al., "Tumor necrosis, cachexia, shock, and inflammation: a common mediator," Annual Review of Biochemistry, 57:505-518 (1988).
Bird et al., "Single-chain antigen-binding proteins," Science, 242(4877):423-426 (1988).
Boyle et al., "A novel monoclonal human IgM autoantibody which binds recombinant human and mouse tumor necrosis factor-alpha," Cell Immunology, 152(2):556-568 (1993).
Boyle et al., "The B5 monoclonal human autoantibody binds to cell surface TNF alpha on human lymphoid cells and cell lines and appears to recognize a novel epitope," Cell Immunology, 152(2):569-581 (1993).
Cada et al. "Adalimumab", Hospital Pharmacy, 38,6:568-580 (2003).
Carpenter et al., "Rational Design of Stable Lyophilized Protein Formulations: Some Practical Advice" Pharmaceutical Research, 14(8):969-975 (1997).

(56) References Cited

OTHER PUBLICATIONS

Carpenter, et al., "Chapter 7: Freezing- and Drying-Induced Perturbations of Protein Structure and Mechanisms of Protein Protection by stabilizing Additives," Freeze-Drying/Lyophilization of Pharmaceutical and Biological Products, 2d ed., 167-197 (2004).
Carpenter, et al., "Inhibition of Stress-Induced Aggregation of Protein Therapeutics," Methods in Enzymology, 309:235-255 (1999).
Certificate of Amalgamation submitted by Patentee during Opposition of EP1528933 (Aug. 5, 2003).
Chang et al., "Surface-Induced Denaturation of Proteins during Freezing and Its Inhibition by Surfactants", Journal of Pharmaceutical Sciences, 85(12):1325-1330 (1996).
Chi, et al., "Physical Stability of Proteins in Aqueous Solution: Mechanism and Driving Forces in Nonnative Protein Aggregation," Pharmaceutical Research, 20(9): 1325-1336 (2003)
Chiodi et al., "Isoelectric focusing of monoclonal immunoglobulin G, A and M followed by detection with the avidin-biotin system", Electrophoresis, 6:124-128 (1985).
Citric Acid, ACS Reagent, Sigma-Aldrich (Nov. 20, 2014).
Cleland et al., "A Specific Molar Ratio of Stabilizer to Protein is Required for Storage Stability of a Lyophilized Monoclonal Antibody," Journal of Pharmaceutical Sciences, 90(3):310-321 (2001).
Cleland et al., "The Development of Stable Protein Formulations: A Close Look at Protein Aggregation, Deamidation, and Oxidation", Critical Reviews in Therapeutic Drug Carrier Systems. 10(4):307-377 (1993).
Coriolis Pharma Technical Report, "Phase 3: Side by Side Comparison of 'Citrate Formulation' and 'Claim Formulation'—Stability Study" (Jan. 10, 2014), submitted by Patentee during Opposition of EP1528933.
Corrected Sequence Listing filed Feb. 16, 2005 in U.S. Pat. No. 8,216,583 submitted during Opposition of EP1528933.
Davis et al., "Structure of human tumor necrosis factor alpha derived from recombinant DNA", Biochemistry, 26(5):1322-1326 (1987).
Decision to Refuse Application submitted during Opposition of EP1528933 (Dec. 20, 2010).
Declaration of Theodore W. Randolph, Ph.D. U.S. Pat. No. 8,916,157 (Jun. 25, 2015) (182 pages).
Declaration of Theodore W. Randolph, Ph.D. U.S. Pat. No. 8,916,158 (Jun. 25, 2015) (179 pages).
Definitions of "phosphate buffer" and "citrate buffer" according to Wikipedia (downloaded Dec. 20, 2012).
den Broeder et al. Long term anti-tumour necrosis factor a monotherapy in rheumatoid arthritis: effect on radiological course and prognostic value of markers of cartilage turnover and endothelial activation, Annals of the Rheumatic Diseases, 61:311-318 (2002).
Duhamel et al., "pH gradient elution of human IgG1, IgG2 and IgG4 from protein A-sepharose," Journal of Immunogical Methods, 31(3-4):211-217 (1979).
Eason et al., "Inhibition of the effects of TNF in renal allograft recipients using recombinant human dimeric tumor necrosis factor receptors," Transplantation, 59(2):300-305 (1995).
Elliot et al., "Randomised double-blind comparison of chimeric monoclonal antibody to tumour necrosis factor alpha (cA2) versus placebo in rheumatoid arthritis," Lancet, 344(8930):1105-1110 (1994).
Elliott, "Repeated therapy with monoclonal antibody to tumour necrosis factor alpha (cA2) in patients with rheumatoid arthritis," Lancet, 344(8930):1125-1127 (1994).
Ewert et al., "Biophysical properties of human antibody variable domains," Journal of Molecular Biology, 325(3):531-553 (2003)
Expert Opinion of Professor Gerhard Winter (Jan. 13, 2014), submitted by Patentee during Opposition of EP1528933.
Exposure Factors Handbook (E.P.A. 1997) (50 pages).

Fava et al., "Critical role of peripheral blood phagocytes and the involvement of complement in tumour necrosis factor enhancement of passive collagen-arthritis," Clinical and Experimental Immunology, 94(2):261-266 (1993).
Felver et al., "Plasma tumor necrosis factor alpha predicts decreased long-term survival in severe alcoholic hepatitis," Alcoholism, Clinical and Experimental Research, 14(2):255-259 (1990).
Fendly et al., "Murine monoclonal antibodies defining neutralizing epitopes on tumor necrosis factor," Hybridoma, 6(4):359-370 (1987).
Fiedler: 'Lexikon der Hifsstoffe', 1996, Editio Cantor Verlag Aulendorf.
Fietze et al., "Cytomegalovirus infection in transplant recipients. The role of tumor necrosis factor," Transplantation, 58(6):675-680 (1994).
Fomsgaard et al., "Auto-antibodies to tumour necrosis factor alpha in healthy humans and patients with inflammatory diseases and gram-negative bacterial infections," Scandinavian Journal of Immunology, 30(2):219-223 (1989).
Giroir et al., "Inhibition of tumor necrosis factor prevents myocardial dysfunction during burn shock," American Journal of Physiology, 267(1 Pt 2):H118-H124 (1994).
Griffiths et al., "Human anti-self antibodies with high specificity from phage display libraries," EMBO Journal, 12(2):725-734 (1993).
Grounds of Appeal filed by Applicant submitted during Opposition of EP1528933 (Apr. 29, 2011).
Ha, et al., "Peroxide Formation in Polysorbate 80 and Protein Stability," Journal of Pharmaceutical Sciences, 91(10):2252-2264 (2002).
Hahn et al., "Use of monoclonal antibodies to a human cytotoxin for its isolation and for examining the self-induction of resistance to this protein," PNAS, 82(11):3814-3818 (1985).
Hamilton, "The Human IgG Subclass," Asthma and Allergry Center, Johns Hopkins University, Calbiochem-Novabiochem Corporation (2001) (64 pages).
Hansen et al., "The role of tumor necrosis factor-alpha in acute endotoxin-induced hepatotoxicity in ethanol-fed rats," Hepatology, 20(2):461-474 (1994).
Harris et al., "Commercial manufacturing scale formulation and analytical characterization of therapeutic recombinant antibodies", Drug Development Research., 61(3):137-154 (2004).
Helms et al., "Destabilizing loop swaps in the CDRs of an immunoglobulin VL domain," Protein Science, 4(10):2073-2081 (1995).
Herceptin (trastuzumab) [package insert]. South San Francisco, CA: Genentech, Inc.(1998) (3 pages).
Hillgren et al., "Protection mechanism of Tween 80 during freeze-thawing of a model protein," International Journal of Pharmaceutics, 237:57-69 (2002).
Hirai et al., "Production and characterization of monoclonal antibodies to human tumor necrosis factor," Journal of Immunological Methods, 96(1):57-62 (1987).
Holliger et al., ""Diabodies": small bivalent and bispecific antibody fragments," PNAS, 90(14):6444-6448 (1993).
Holt et al., "Domain antibodies: proteins for therapy," Trends in Immunology, 21(11 ):484-490 (1993).
Hovgaard & Frokjaer (eds) "Pharmaceutical Formulation Development of Peptides and Proteins", CRC Press 1999.
Humira (adalimumab) Product Insert, Dec. 20, 2002 (16 pages).
Humira, IMS Product Monographs, Sep. 2002 (4 pages).
Humphreys, "Top 200 Medicines—Special Report," Pharmalive (Aug. 12, 2015), http://www.pharmalive.com/specialreport-top-200-medicines/ (5 pages).
Hussain et al., "Hepatic expression of tumour necrosis factor-alpha in chronic hepatitis B virus infection," Journal of Clinical Pathology, 47(12):1112-1115 (1994).
Huston et al., "Protein engineering of antibody binding sites: recovery of specific activity in an anti-digoxin single-chain Fv analogue produced in *Escherichia coli*," PNAS, 85(16):5879-5883 (1988).
International Preliminary Examination Report for Application No. PCT/IB03/04502, dated Feb. 14, 2005.

(56) References Cited

OTHER PUBLICATIONS

International Search Report for Application No. PCT/IB03/04502 dated May 26, 2004.
IPR2015-01514, Patent Owner's Preliminary Response, dated Oct. 19, 2015 (70 Pages).
IPR2015-01517, Patent Owner's Preliminary Response, dated Oct. 19, 2015 (70 Pages).
Johnson et al., "Kabat Database and its applications: 30 years after the first variability plot", Nucleic Acids Research, 28(1):214-218 (2000).
Johnsson et al., "Comparison of methods for immobilization to carboxymethyl dextran sensor surfaces by analysis of the specific activity of monoclonal antibodies," Journal of Molecular Recognition, 8(1-2):125-131 (1995).
Johnsson et al., "Immobilization of proteins to a carboxymethyldextran-modified gold surface for biospecific interaction analysis in surface plasmon resonance sensors," Analytical Biochemistry, 198(2):268-277 (1991).
Jones et al., "Analysis of polypeptides and proteins," Advanced Drug Delivery Reviews, 10:29-90 (1993).
Jones et al., "Structure of tumour necrosis factor," Nature, 338(6212):225-228 (1989).
Jönsson et al., "Introducing a biosensor based technology for real-time biospecific interaction analysis," Annales de Biologie Clinque (Paris), 51(1):19-26 (1993).
Jönsson et al., "Real-time biospecific interaction analysis using surface plasmon resonance and a sensor chip technology," Biotechniques, 11(5):620-627 (1991).
Kamerzell, et al., "Increasing IgG Concentration Modulates the Conformational Heterogeneity and Bonding Network that Influence Solution Properties," Journal for Physical Chemistry, 113:6109-6118 (2009).
Kempeni et al., "Preliminary results of early clinical trials with the fully human anti-TNFα monoclonal antibody D2E7", Annals of Rheumatic Diseases, 58:(Suppl. I) 170-172 (1999).
Kempeni, "Update on D2E7: a fully human anti-tumor necrosis factor a Monoclonal antibody," Annals of the Rheumatic Diseases, 59(suppl I):i44-i45 (2000).
Kineret (anakinra) [package insert]. Thousand Oaks, CA: Amgen Inc. (2001) (13 pages).
King, "The Best Selling Drugs of All Time; Humira Joins the Elite," Forbes, Jan. 28, 2013, 9:58 AM), http://www.forbes.com/sites/simonking/2013/01/28/the-best-sellingdrugs-of-all-time-humira-joins-the-elite/print/ (4 pages).
Kipriyanov et al., "Recombinant single-chain Fv fragments carrying C-terminal cysteine residues: production of bivalent and biotinylated miniantibodies," Molecular Immunology, 31(14):1047-1058 F(1994).
Kipriyanov et al., "Single-chain antibody streptavidin fusions: tetrameric bifunctional scFv-complexes with biotin binding activity and enhanced affinity to antigen," Human Antibodies and Hybridomas, 6(3):93-101 (1995).
Knight et al., "Construction and initial characterization of a mouse-human chimeric anti-TNF antibody," Molecular Immunology, 30(16):1443-1453 (1993).
Konig et al., "Tumor necrosis factor alpha and interleukin-1 stimulate bone resorption in vivo as measured by urinary [3H]tetracycline excretion from prelabeled mice," Journal of Bone and Mineral Research, 3(6):621-627 (1988).
Krishnamurthy, et al., "The Stability Factor: Importance in Formulation Development," Current Pharmaceutical Biotechnology, 3:361-371 (2002).
Krishnan, et al., "Chapter 16: Development of Formulations for Therapeutic Monoclonal Antibodies and Fc Fusion Proteins," Formulation and Process Development Strategies for Manufacturing Biopharmaceuticals, 383-427 (2010).
Lee, et al., "Toward aggregation-resistant antibodies by design," Trends in Biotechnology, 31(11):612-620 (2013).
Lerner et al., "Tumor necrosis factors alpha and beta can stimulate bone resorption in cultured mouse calvariae by a prostaglandin-independent mechanism," Journal of Bone and Mineral Research, 8(2):147-155(1993).
Leusch et al., "Failure to demonstrate TNF alpha-specific autoantibodies in human sera by ELISA and western blot," Journal of Immunological Methods , 139(1):145-147 (1991).
Levine, "The Use of Surface Tension Measurements in the Design of Antibody-Based Product Formulations", Journal of Parenteral Science and Technology, 45(3):160-165 (1991).
Liang et al., "Production and characterization of monoclonal antibodies against recombinant human tumor necrosis factor/cachectin," Biochemical and Biophysical Research Communications, 137(2):847-854 (1986).
Lidbury et al., "The effect of enhancing antibodies on TNF interactions with its specific receptor: consequences for in vitro TNF antiviral activity," Biotechnology Therapies, 5(1&2):27-45 (1994).
Liu et al., "The significance of changes in serum tumour necrosis factor (TNF) activity in severely burned patients," Burns, 20(1):40-44 (1994).
Lorenz, "Technology evaluation: Adalimumab, Abbott Laboratories" Current Opinion in Molecular Therapeutics, 4(2):185-190 (2002).
MacDonald et al., "Tumour necrosis factor-alpha and interferon-gamma production measured at the single cell level in normal and inflamed human intestine," Clinical and Experimental Immunology, 81(2):301-305 (1990).
Manning et al., "Stability of Protein Pharmaceuticals", Pharmaceutical Research, 6(11):903-918 (1989).
McCauley et al., "Altered cytokine production in black patients with keloids," Journal of Clinical Immunology, 12(4):300-308 (1992).
McClain et al., "Increased tumor necrosis factor production by monocytes in alcoholic hepatitis," Hepatology, 9(3):349-351 (1989).
Mithal, "A Textbook of Pharmaceutical Formulation: Surfactants, the Interfacial Phenomenon," Chapter 6, pp. 49-62 , Oct. 9, 1980.
Moeller et al., "Monoclonal antibodies to human tumor necrosis factor alpha: in vitro and in vivo application," Cytokine, 2(3):162-169 (1990).
Nail et al. "Development and Manufacture of Protein Pharmaceuticals," (Kluwer Academic/Plenum Publishers, New York, pp. 47-127 (Jun. 30, 2002).
Nema et al., "Excipients and Their Use in Injectable Products", PDA Journal of Pharmaceutical Science and Technology, 51:166-171 (1997).
Neulasta (pegfilgrastim) [package insert]. Thousand Oaks, CA: Amgen Inc. (2002) (29 pages) http://www.accessdata.fda.gov/drugsatfda_docs/nda/2002/125031_0000_NeulastaTOC.cfm (identifying biologics license approval on Jan. 31, 2002).
Neupogen (filgrastim) [package insert]. Thousand Oaks, CA: Amgen Inc.; (1998) (27 pages).
Nishida, et al., "Characterization of novel murine anti-CD20 monoclonal antibodies and their comparison to 2B8 and c2B8 (rituximab)," International Journal of Oncology, 31:29-40 (2007).
Notice of opposition of European Patent EP1528933, submitted by Alfred E. Tiefenbacher, Feb. 1, 2013 (with English Translation).
Notice of opposition of European Patent EP1528933, submitted by Dr. Ulrich Storz, Feb. 1, 2013.
Notice of opposition of European Patent EP1528933, submitted by Teva Pharmaceutical Industries Ltd., Feb. 4, 2013.
Notice of opposition of European Patent EP1528933, submitted by William Edward Bird, Jan. 31, 2013.
Ohnishi, et al., "The Effect of Nonionic Surfactant Structure on Hemolysis," Journal of the American Oil Chemists' Society, 70(7):679-684 (1993).
Old, "Tumor necrosis factor (TNF)," Science, 230(4726):630-632 (1985).
Paborij et al., "Chemical and Physical Stability of Chimeric L6, a Mouse-Human Monoclonal Antibody," Pharmaceutical Research, 11, 5:764-771 (1994).
Patentee Priority Application Assignment in U.S. Appl. No. 10/222,140 submitted during Opposition of EP1528933 (Dec. 12, 2002).

(56) References Cited

OTHER PUBLICATIONS

Patentee's Compilation Record submitted during Opposition of EP1528933 (Jan. 10, 2014).
Patentee's Recordation of Name Change in PCT/IB2003/004502 submitted by Patentee during Opposition of EP1528933 (Jan. 18, 2005).
Patentee's Request for Name Change submitted during Opposition of EP1528933 (Dec. 1, 2005).
Patentee's Response on 71(3) Communication submitted during Opposition of EP1528933, plus Request to Correct the Sequence Listing (Feb. 15, 2012).
Patentee's Response submitted during Oppositions of EP1528933 (Jan. 17, 2014).
PBS recipe as published by Cold Spring Harbor Protocols (downloaded Dec. 19, 2012).
Pearlman et al., "Analysis of Protein Drugs," Peptide and Protein Drug Delivery, Marcel Dekker, Inc., pp. 247-301 (1991).
Pegintron (peginterferon alpha-2b) [package insert] Kenilworth, NJ: Schering Corporation; 2001 (28 pages).
Pennica et al., "Human tumour necrosis factor: precursor structure, expression and homology to lymphotoxin," Nature, 312(5996):724-729 (1984).
Pennington et al., "Polyclonal and monoclonal antibody therapy for experimental Pseudomonas aeruginosa pneumonia", Infection and Immunity, 54(1):239-244 (1986).
Perchiacca et al., "Engineering Aggregation Resistant Antibodies," Annual Review of Chemical and Biomolecular Engineering, 3:263-286 (2012).
Petition for Inter Partes Review, Amgen Inc. v. AbbVie Biotechnology Ltd., U.S. Pat. No. 8,916,157, Jun. 26, 2015 (70 pages).
Petition for Inter Partes Review, Amgen Inc. v. AbbVie Biotechnology Ltd., U.S. Pat. No. 8,916,158, Jun. 26, 2015 (69 pages).
Pharmaceuticals, The Science of Dosage Form Design, (Michael E. Aulton ed., 2d ed. (2002) (15 pages).
Poljak, "Production and structure of diabodies," Structure, 2(12):1121-1123 (1994).
Product Information Issued by the European Medicines Agency (EMA) with Respect to adalimumab/Humira®—EMEA/H/C/000481-II/0094, Aug. 2012 (212 pages).
Randolph, et al., "Engineering Challenges of Protein Formulations," American Institute of Chemical Engineers, 51(8):1902-1907 (2007).
Rankin et al., "The therapeutic effects of an engineered human anti-tumour necrosis factor alpha antibody (CDP571) in rheumatoid arthritis," British Journal of Rheumatology, 34(4):334-342 (1995).
Rational Design of Stable Protein Formulations: Theory and Practice (Carpenter and Manning, ed., Apr. 30, 2002) (222 pages).
Rau, "Adalimumab (a fully human anti-tumour necrosis factor alpha monoclonal antibody) in the treatment of active rheumatoid arthritis: the initial results of five trials," Annals of Rheumatic Disease, 61(Suppl II):ii70-ii73 (2002).
Register Extract of U.S. Appl. No. 10/222,140 submitted during Opposition of EP1528933 (downloaded Dec. 7, 2012).
Remicade (infliximab) [package insert]. Malvern, PA: Centocor, Inc. (1998) (12 pages).
Remington: The Science and Practice of Pharmacy (Alfonso Gennaro ed., 20th ed. 2000) (7 pages).
Reply to the Summons to attend oral proceedings on Sep. 8 to 10, 2015 pursuant to Rule 115(1) EPC filed by Dr. Ulrich Storz during Opposition of European Patent EP1528933.
Result of Consultation of Oct. 28, 2010 by the EPO submitted during Opposition of EP1528933 (Nov. 3, 2010).
Rouet, et al., "Stability engineering of the human antibody repertoire," FEBS Letters, 588:269-277 (2014).
Russel et al., "Targets for sepsis therapies: tumor necrosis factor versus interleukin-1," Current Opinion in Biotechnology, 4:714-721 (1993).
Salfeld, "Generation of Fully Human Anti-TNF Antibody D2E7," Arthritis and Rheumatism, 41(9):S57, Abstract 147 (1998).
Salinas, et al., "Understanding and modulating opalescence and viscosity in a monoclonal antibody formulation", Journal of Pharmaceutical Sciences, 99(1):82-93 (2010).
Santora et al., "Characterization of recombinant human monoclonal tissue necrosis factor-alpha antibody using cation-exchange HPLC and capillary isoelectric focusing," Analytical Biochemistry, 275(1):98-108 (1999).
Santora et al., "Determination of Recombinant Monoclonal Antibodies and Noncovalent Antigen TFN-Alpha Timer Using Q-TOF Mass Spectrometry," Spectroscopy, 17(5):50-57 (2002).
Scales et al., "Hepatic ischemia/reperfusion injury: importance of oxidant/tumor necrosis factor interactions," American Journal of Physiology, 267(6 Pt 1):G1122-G1127 (1994).
Schein, "Solubility as a Function of Protein Structure and Solvent Components", Nature Biotechnology, 8:308-317 (1990).
Sequence Listing filed with U.S. Appl. No. 10/222,140 submitted during Opposition of EP1528933 (May 6, 2003).
Serrick et al., "The early release of interleukin-2, tumor necrosis factor-alpha and interferon-gamma after ischemia reperfusion injury in the lung allograft," Transplantation, 58(11):1158-1162 (1994).
Shankar et al., "Evaluation of the role of second messenger systems in tumor necrosis factor-stimulated resorption of fetal rat limb bones," Bone, 14(6):871-876 (1993).
Sheron et al., "Increased production of tumour necrosis factor alpha in chronic hepatitis B virus infection," Journal of Hepatology, 12(2):241-245 (1991).
Shimazato et al., "Suppression of Tumor Necrosis Factor Alpha Production by a Human Immunoglobulin Preparation for Intravenous Use", Infection and Immunity, 58:1384-1390 (1990).
Sivasai et al., "Cytomegalovirus immune globulin intravenous (human) administration modulates immune response to alloantigens in sensitized renal transplant candidates", Clinical & Experimental Immunology, 119:559-565 (2000).
Summons to Oral Proceedings with Annex submitted during Opposition of EP1528933 (Apr. 6, 2010).
Sun et al., "Bowel necrosis induced by tumor necrosis factor in rats is mediated by platelet-activating factor," Journal of Clinical Investigation, 81(5):1328-1331 (1998).
Suthanthiran et al., "Renal Transplantation," New England Journal of Medicine, 331(6):365-375 (1994).
Taylor et al., "A transgenic mouse that expresses a diversity of human sequence heavy and light chain immunoglobulins," Nucleic Acids Research, 20(23):6287-6295 (1992).
Test Report as cited during prosecution of related European Patent No. EP1528933, grant date of Sep. 28, 2012 (27 pages).
The Merck Index, Encyclopedia of Chemicals, Drugs, and Biolgicials, 14th Edition, Citric Acid, p. 389, 2006.
Third Party Observations submitted during Opposition of EP1528933 (Aug. 26, 2011).
Timmerman, "Abbott's Humira, the 3rd-in-Class Drug That Toppled Lipitor as No. 1," Xconomy (Apr. 16, 2012), http://www.xconomy.com/national/2012/04/16/abbotts-humira-the-3rd-in-class-drug-that-toppled-lipitor-as-no-1/ (6 pages).
Tracey et al., "Shock and tissue injury induced by recombinant human cachectin," Science, 234(4775):470-474 (1986).
Tracey et al., "Tumor necrosis factor: a pleiotropic cytokine and therapeutic target," Annual Review of Medicine, 45:491-503 (1994).
U.S. Appl. No. 11/437,602 (now U.S. Pat. No. 8,858,935) (Amgen), Jun. 25, 2009 Declaration by Dr. Grace C. Chu (4 pages).
U.S. Appl. No. 11/437,602 (now U.S. Pat. No. 8,858,935) (Amgen), Jun. 25, 2009 Office Action Response (18 pages).
U.S. Appl. No. 11/784,538 (now U.S. Pat. No. 7,648,702) (Amgen), Jul. 24, 2009 Office Action Response (52 pages).
U.S. Appl. No. 13/401,496 (now U.S. Pat. No. 8,828,947) (Immunex/Amgen), Apr. 21, 2014 Office Action Response (7 pages).
U.S. Appl. No. 13/521,999 (now U.S. Pat. No. 8,883,151) (Amgen), Dec. 3, 2013 Office Action Response (9 pages).
United States Pharmacopeia and National Formulary (USP 24-NF 19) Rockville, MD: United States Pharmacopeia Convention (2000) (25 pages).

(56) References Cited

OTHER PUBLICATIONS

Van De Weert, et al., "Chapter 6: Physical Instability of Peptides and Proteins," Pharmaceutical Formulation Development of Peptides and Proteins, 107-129 (2012) (129 pages).
Van Der Poll et al., "Activation of coagulation after administration of tumor necrosis factor to normal subjects," New England Journal of Medicine, 322(23):1622-1627 (1990).
Van Der Poll et al., "Comparison of the early dynamics of coagulation activation after injection of endotoxin and tumor necrosis factor in healthy humans," Progress in Clinical and Biological Research, 367:55-60 (1991).
Van Dullemen et al., "Treatment of Crohn's disease with anti-tumor necrosis factor chimeric monoclonal antibody (cA2)," Gastroenterology, 109(1):129-135 (1995).
Vasilli, "The pathophysiology of tumor necrosis factors," Annual Review of Immunology, 10:411-452 (1992).
Voigt et al., "Textbook of Pharmaceutical Technology," VCH, pp. 384, 385, 388, 389, 392, 393 (1987).
Voigt, "Textbook of pharmaceutical technology" VCH, 384, 394, 395 (1987) (in German).
Wang et al. "Instability, Stabilization, and Formulation of Liquid Protein Pharmaceuticals," International Journal of Pharmaceutics, 185:129-188 (1999).
Wang et al., "Antibody Structure, Instability, and Formulation," Journal of Pharmaceutical Sciences, 96(1):1-26 (2007).
Wang, "Lyophilization and development of solid protein pharmaceuticals," International Journal of Pharmaceutics, I(203), 1-2:1-60 (2000).
Ward et al., "Binding activities of a repertoire of single immunoglobulin variable domains secreted from *Escherichia coli*," Nature, 341(6242):544-546 (1989).
Weinblatt et al., "Adalimumab, a fully human anti-tumor necrosis factor alpha monoclonal antibody, for the treatment of rheumatoid arthritis in patients taking concomitant methotrexate: the ARMADA trial," Arthritis and Rheumatism, 48(1):35-45 (2003).
Yao et al., "The potential etiologic role of tumor necrosis factor in mediating multiple organ dysfunction in rats following intestinal ischemia-reperfusion injury," Resuscitation, 29(2):157-168(1995).
Zenapax (daclizumab) [package insert]. Nutley, NJ: Hoffmann-LaRoche, Inc. (1997) (2 pages) 1997.
Zhao et al., "Recent U.S. Patents on Protein Drug Formulation: 2000-2007," Recent Patents on Drug Delivery and Formulation, 2(3):200-208(9) (2008).
ChEMBL, Compound Report Card, downloaded May 6, 2016, https://www.ebi.ac.uk/chembl/compound/inspect/CHEMBL1201580 (2 pages).
DrugBank: Adalimumab, downloaded Jun. 29, 2016, http://www.drugbank.ca/drugs/DB00051 (9 pages).
Fry, "Tools and Technologies for Immunogenicity and Allergenicity Risk Management," presentation slides shown on the HESI PATC Symposium on Sensitizing Properties of Proteins, Apr. 11-13, 2012 (12 pages).
NextMove Software, "Validity checking antibody sequence data," downloaded Jun. 29, 2016, https://nextmovesoftware.com/blog/2014/07/07/validity-checkingantibody-sequence-data/ (3 pages).
Patentee's Application for Patent Term Extension for U.S. Pat. No. 6,090,382, dated Feb. 27, 2003 (23 pages).
Protein Data Bank in Europe. Adalimumab, downloaded Jul. 12, 2016, https://www.ebi.ac.uk/pdbe/entry/search/index?text:%20Adalimumab (8 pages).
Recherche CAS Nr. 331731-18-1, Printout of search results using the term "D2E7" in the CAS registry, Jun. 27, 2016 (German Language) (4 pages).
Scheffler et al., "Improving Intact Antibody Characterization by Orbitrap Mass Spectrometry," Thermo Scientific Poster Note BioPharma 2013_PN63712_E_11/13S (2013) (6 pages).
"Adalimumab Cambridge Antibody Technology clinical data," R&D Focus Drug News (Jul. 2, 2001) (1 page).
"Antibody Production; Liquid Formulation with 2-Year Shelf Life Developed," 12, Immunotherapy Weekly, Feb. 13, 2000 (2 pages).
"BASF moves into Phase III with D2E7," MarketLetter (Feb. 14, 2000) (1 page).
"CAT/Abbott's D2E7 in Crohn's disease trials," Marketletter (Feb. 19, 2001) (3 pages).
Abbott Laboratories, Earnings Conference Call transcript (Apr. 9, 2002) (22 pages).
Abbott Laboratories, Earnings Conference Call transcript (Jul. 11, 2002) (11 pages).
Adalimumab—DrugBank, https://www.drugbank.ca/drugs/DB00051, downloaded Jan. 24, 2017 (2 pages).
Adalimumab Heavy Chain in PDB, https://www.ebi.ac.uk/pdbe/entry/pdb/4nyl/protein/2 downloaded Jan. 18, 2017(2 pages).
Adalimumab Light Chain in PDB, https://www. ebi .a c. uk/pdbe/entry/pcfb14nyl/protein/1, downloaded Jan. 24, 2017 (2 pages).
Adalimumab, Search Results (2) https://www.ebi.ac.uk/ebisearch/search.ebi?db=uniref100&t=adalimumab&f=TAXONOMY:9606, downloaded Jan. 18, 2017 (1 page).
Akers et al., "Formulation Development of Protein Dosage Forms," Development and Manufacture of Protein Pharmaceuticals, Kluwer Academic/Plenum Publishers, Chapter 2:47-127 (2002) (82 pages).
Akers et al., "Peptides and Proteins as Parenteral Solutions," Pharmaceutical Formulation Development of Peptides and Proteins, Taylor & Francis, Chapter 8:45-177 (1999) (50 pages).
Annex to the communication of the Examination Division of Mar. 27, 2016 for the divisional case EP-10182610 to the Opposed Patent (7 Pages).
Arakawa et al., "Factors Affecting Short-Term and Long-Term Stabilities of Proteins", Advanced Drug Delivery Reviews, 10:1-28 (1993).
Ash, "Chemicals in Compliance with Pharmaceutical Standards: Inactive Ingredient Guide," Handbook of Pharmaceutical Additives 1027-35 (2002) (11 pages).
Cambridge Antibody Technology Group. Press Release: "CAT Announces Results for Year Ended Sep. 1998" (7 pages).
Cambridge Antibody Technology Group. Press Release: "Impressive Clinical Data with CAT/BASF Human Antibody in Rheumatoid Arthritis" (1998) (2 pages).
Cambridge Antibody Technology. Press Release "Clinical Data Presented on CAT and BASF Pharma's D2E7 Monoclonal Antibody." (PR Newswire) (1999) (3 pages).
Campath Label (PDR) (May 2001) (6 pages).
Canfield et al., "The binding affinity of human IgG for its high affinity Fc receptor is determined by multiple amino acids in the CH2 domain and is modulated by the hinge region," Journal of Experimental Medicine, 173:(6):1483-1491 (1991).
Carimune NF, Package Insert (Aug. 2013) (19 pages).
Carpenter, J. & Manning, M., eds., Rational Design of Stable Protein Formulations, Theory and Practice, Pharmaceutical Biotechnology, vol. 13 (2002) ("Carpenter") (222 pages).
Ceredase Label, Oct. 2004 (6 pages).
Dawson et al., "Data for Biochemical Research," (3d edition, 1986) (4 pages).
Duvvuru et al., "Development of a Subcutaneous Liquid Formulation at 100 Mg/ML for a Humanized Monoclonal Antibody," 2001 AAPS5 Annual Meeting and Exposition, Colorado Convention Center, Denver, CO, Oct. 21-25, 2001 (1 page).
EBI Search, Adalimumab in UniRef100, https://www.ebi.ac.uk/ebisearch/search.ebi?db=uniref100&t=adalimumab, downloaded Jan. 18, 2017 (2 pages).
EBI Search, Adalimumab, https://www.ebi.ac.uk/ebisearch/search.ebi?guery=adalimumab&submit=&db=allebi&requestFrom=global-masthead, downloaded Jan. 18, 2017 (4 pages).
Email from the STN FIZ-Helpdesk of Jan. 12, 2017 confirming the entry date "ED" (with English Translation) (3 pages).
ENBREL® (etanercept), dated Nov. 1998 (6 pages).
FDA Guideline for Submitting Documentation for the Stability of Human Drugs and Biologics (Feb. 1987) (62 pages).
FDA Guideline for Submitting Supporting Documentation in Drug Applications for the Manufacture of Drug Substances (Feb. 1987) (48 pages).
Fiedler, Encyclopedia of Excipients (5th Ed., 2002) (7 pages).
Gamimune N 10% Label (1999) (3 pages).

(56) References Cited

OTHER PUBLICATIONS

Gamimune N 5% Label (Jun. 1999) (4 pages.).
Gamimune PDF Cutter (1986) (3 pages).
Gammargard Label (PDR)) (Jan. 2001) (3 Pages).
Gammar-P I.V. (Aug. 200) (2 pages).
Gamunex-C Package Insert (Dec. 2015) (53 pages).
Gardulf et al., "Safety of rapid subcutaneous gammaglobulin infusions in patients with primary antibody deficiency," Immunodeficiency 4(1-4):81-84 (1993).
Goddard, "Therapeutic Proteins—A Pharmaceutical Perspective," Advanced Drug Delivery Reviews, 6:103-131 (1991).
Gombotz el al., "Stability, Characterization, formulations and Delivery System Development for Transforming Growth Factor-Beta1," Formulation, Characterization and Stability of Protein Drugs: Case Hislories, Kluwer Academic Publishers, Chapter 4:219-245 (1996) (53 pages).
Gorgani et al., "Differential binding of histidine-rich glycoprotein (HRG) to human IgG subclasses and IgG molecules containing kappa and lambda light chains," The Journal of Biological Chemistry, 274(42):29633-29640 (1999).
Haller, "Converting Intravenous Dosing to Subcutaneous Dosing With Recombinant Human Hyalu ronidase", Pharmaceutical Technology, 31(10) (2007) (8 pages).
Hansson, "Correlation between amount of aggregates formed on freezing of immunoglobulin G and protein concentration," Acta Chemica Scandivavica , 23(5):1828-1829 (1969).
Hu et at., "Comparison of the inhibition mechanisms of adalimumab and infliximab in treating tumor necrosis factor α-associated diseases from a molecular view", Journal of Biological Chemistry, 288(38):27059-27067 (2013).
ICH Harmonised Tripartite Guidelines, Stability Testing of New Drug Substances and Products Q1A, Jan. 1, 1998 (14 pages).
Kaisheva et al., "Development of a Subcutaneous Liquid Formulation at 100 mg/ml for a Humanized Monoclonal Antibody Using Experimental Design Techniques," AAPS Annual Meeting and Exposition, Ernest N. Morial Convention Center, New Orleans, LA, Nov. 14-18, 1999 (1 page).
Kaufman et al., "Subcutaneous Compared with Intravenous Epoetin in Patients Receiving Hemodialys is," New England Journal of Medicine, 339(9):575-583 (1998).
Keystone et al., "The Armada Trial: A Double-Blind Placebo Controlled Trial of the Fully Human Anti-TNF Monoclonal Antibody, Adalimumab (D2E7), in Patients with Active RA on Methotrexate (MTX)," Arthritis & Rheumatology, 44(suppl):S213 (2001) (4 pages).
Kibbe, "Manitol" and "Polyoxyethylene sorbitan fatty acid esters," *Handbook of Pharmaceutical Excipients*, 3$^{rd}$ Edition, 2000, 324-328 and 416-419.
Kreilgaard et al., "Effect of Tween 20 on freeze-thawing- and agitation-induced aggregation of recombinant human factor XIII," Journal of Pharmaceutical Sciences, 87(12):1597-1603 (1998).
Lemtrada® (alemtuzumab) (May 2001) (36 pages).
Liu et al., "Excipients Commonly Used in Pharmaceutical Preparation," Tianjin Science & Technology Translation & Publishing Corporation (1994) (41 pages).
MacKenzie et al., "Effect of C lambda-C kappa domain switching on Fab activity and yield in *Escherichia coli*: synthesis and expression of genes encoding two anti-carbohydrate Fabs," Biotechnology (NY), 12(4):390-395 (1994).
Montano et al., "Influence of the isotype of the light chain on the properties of IgG," The Journal of Immunology, 168(1):224-231 (2002).
Mylotarg Label (PDR) (Apr. 6, 2001) (4 pages).
Mylotarg® (gemtuzumab ozogamicin), dated Jun. 2000 (16 pages).
Myoscint® (imciromab pentetate) (Oct. 1996) (2 pages).
Parkins et al., "The formulation of biopharmaceutical products," Pharmaceutical Science & Technology Today, 3:129-137 (2000).
Physician's Desk Reference (52nd ed., 1998) (2 pages).
Physicians' Desk Reference, 55th Edition, 1314-1316, 1549-1551, 1771-1774, 2303-2307, 2813-2814 (2001) (19 pages).
Physician's Desk Reference: Supplement B (57th ed., 2003) (4 pages).
Polygam Label (PDR) (Jul. 26, 1999) (2 pages).
Pritsch et al., "Can immunoglobulin C(H)1 constant region domain modulate antigen binding affinity of antibodies?," Journal of Clinical Investigation, 98(10)2235-2243 (1996).
Pritsch et al., "Can isotype switch modulate antigen-binding affinity and influence clonal selection?," European Journal of Immunology, 2000, 30: 3387-3395 (2000).
Rau et al. "Long-Term Treatment With the Fully Human Anti-TNF-Antibody D2E7 Slows Radio-Graphic Disease Progression in Rheumatoid Arthritis," Arthritis & Rheumatology, 42(9):S400 (Abstract 1978) (1999) (1 page).
Rau et al., "Effective Combination of the Fully Human Anti-TNF Antibody D2E7 and Methotrexate in Active Rheumatoid Arthritis," Annals of Rheumatic Diseases, 58(1):217 Abstract 907 (1999) (3 pages).
Rau et al., "Experiences with D2E7," Akt Rheumatology, 25:83-88 (2000).
Rau et al., "Long-Term Efficacy and Tolerability of Multiple I.V. Doses of the Fully Human Anti-TNF-Antibody D2E7 in Patients with Rheumatoid Arthritis," Arthritis & Rheumatology, 41(9):S55 (Abstract 137) (1998) (2 page).
Remicade (infliximab), (Nov. 1999) (57 pages).
Remington: The Science & Practice of Pharmacy (19th ed., 1995) (5 pages).
Remington's Pharmaceutical Sciences, 18th Edition, A.R. Gennaro, Chapter 75:1435-1712 (1990) (280 pages).
Sandoglobulin Label (PDR) (Nov. 1998) (5 pages).
Sarciaux et al., "Effects of buffer composition and processing conditions on aggregation of bovine IgG during freeze-drying," Journal of Pharmaceutical Sciences, 88(12):1354-1361 (1999).
Schattenkirchner et al., "Long-Term Use of the Fully Human Anti-TNF Antibody D2E7 in Combination with Methotrexate in Active Rheumatoid Arthritis," Arthritis & Rheumatology, 43(Suppl. 9), Abstract 968 (Sep. 2000) (5 pages).
Screenshot Services, https://www.ebi.ac.uk/services, undated (1 page).
Simianer et al., "One Year Treatment Results of the Fully Human Anti-TNF Antibody D2E7 in Combination with Methotrexate in Active Rheumatoid Arthritis," Annual European Congress of Rheumatology, Abstract POS 370 (2000) (3 pages).
Simulect (basiliximab) (Jul. 2000) (7 pages).
Simulect Label (PDF) (Mar. 2001) (3 pages).
Stiehm et al., "Slow subcutaneous human intravenous immunoglobulin in the treatment of antibody immunodeficiency: use of an old method with a new product," Journal of Allergy and Clinical Immunology, 101(6):848-849 (1998).
Stoll et al., "Buffers: Principles and Practice," Methods in Enzymology, 182:24-38 (1990).
Synagis Label (PDR) (Dec. 2, 1999) (2 pages).
Synagis® (palivizumab), dated Dec. 1999 (7 pages).
Tani et al., "Single Step Method for the Accurate Concentration Determination of Polysorbate 80," Journal of Chromatography A, 786:99-106 (1997).
Taylor, "Anti-tumor necrosis factor therapies," Current Opinion in Rheumatology, 13(3):164-169 (2001).
The Pharma letter, "Positive Data with CAT, BASF Arthritis drug," MarketLetter (1999) (1 page).
United States Adopted Name (USAN) Drug Finder, entry for adalimumab/D2E7, downloaded Jan. 18, 2017 (2 pages).
van de Putte et al., "One Year Efficacy Results of the Fully Human Anti-TNF Antibody D2e7 in Rheumatoid Arthritis.," Arthritis & Rheumatology, 43(9):5269, Abstract 1218 (2000) (3 pages).
Venoglobulin S 10% Label (PDF) (undated) (1 page).
Voet et al. ,"Chemical Properties of Water," Fundamentals of Biochemistry, 31-38 (1999).

(56) References Cited

OTHER PUBLICATIONS

Weisman et al., "A Dose Escalation Study Designed to Demonstrate the Safety, Tolerability and Efficacy of the Fully Human Anti-TNF Antibody, D2E7, Given in Combination with Methotrexate (MTX) in Patients with Active RA," Arthritis & Rheumatology, 43(Suppl. 9):S391, Abstract 1948 (2000) (5 pages).

Winsor, "Patients Report Drug Has Helped" Worcester Telegram & Gazette (Worcester MA) Apr. 26, 2000: E1 (3 pages).

Witzke et al., "Comparison between subcutaneous and intravenous interleukin-2 treatment in HIV disease," Journal of Internal Medicine, 244(3): 235-240 (1998).

Zevalin (Ibritumomab Tiuxetan), Oct. 2001 (38 pages).

Zevalin Label, Dec. 12, 2001 (38 pages).

Breen et al., "Effect of moisture on the stability of a lyophilized humanized monoclonal antibody formulation," Pharmaceutical Research, 18(9):1345-1353 (2001).

Cleland et al., "Formulation and Delivery of Protein and Peptides: Design and Development Strategies," ACS Symposium Series, American Chemical Society, Chapter 1, pp. 1-19 (1994).

Frenken et al., "Identification of the component part in an epoetin alfa preparation that causes pain after subcutaneous injection," American Journal of Kidney Disease, 22(4):553-556 (1993).

Österberg et al., Development of freeze-dried albumin-free formulation of recombinant factor VIII SQ,: Pharmaceutical Research, 14(7):892-898 (1997).

Österberg et al., "B-domain deleted recombinant factor VIII formulation and stability," Seminars in Hematology, 38(2 Suppl 4):40-43 (2001).

Österberg et al., "Physical state of L-histidine after freeze-drying and long-term storage," European Journal of Pharmaceutical Sciences, 8(4):301-308 (1999).

Raffen et al., Physicochemical consequences of amino acid variations that contribute to fibril formation by immunoglobulin light chains, Protein Science, 8(3):509-517 (1999).

Veys et al., "Chemical Properties of Water," Fundamentals of Biochemistry, John Wiley & Sons, Inc., Section 2-2, 31-38 (1999).

Veys et al., "Pain at the injection site of subcutaneously administered erythropoietin: phosphate-buffered epoetin alpha compared to citrate buffered epoetin alpha and epoetin beta," Clinical Nephrology, 49(1):41-44 (1998).

Wade et al., "Polyoxyethylene Sorbitan Fatty Acid Esters," Handbook of Pharmaceutical Excipients, 2nd Edition, pp. 375-378 (1994).

Wade et al., "Mannitol", Handbook of Pharmaceutical Excipients, 2nd Edition, pp. 294-298 (1994) (6 pages).

Wörn et al., "Mutual stabilization of VL and VH in single-chain antibody fragments, investigated with mutants engineered for stability," Biochemistry, 37(38):13120-13127 (1998).

* cited by examiner

FORMULATION OF HUMAN ANTIBODIES FOR TREATING TNF-ALPHA ASSOCIATED DISORDERS

CROSS-REFERENCE TO RELATED APPLICATIONS

This application is a continuation of U.S. patent application Ser. No. 14/826,357, filed Aug. 14, 2015, now U.S. Pat. No. 9,327,032, which is a continuation of U.S. patent application Ser. No. 14/558,182, filed Dec. 2, 2014, now U.S. Pat. No. 9,114,166, issued Aug. 25, 2015, which is a continuation of U.S. patent application Ser. No. 14/453,490, filed Aug. 6, 2014, now U.S. Pat. No. 8,916,158, issued Dec. 23, 2014, which is a continuation of U.S. patent application Ser. No. 14/322,581, filed Jul. 2, 2014, now U.S. Pat. No. 8,911,741, issued Dec. 16, 2014, which is continuation of U.S. patent application Ser. No. 14/091,938, filed Nov. 27, 2013, now U.S. Pat. No. 8,795,670, issued Aug. 5, 2014, which is a continuation of U.S. patent application Ser. No. 13/471,820, filed May 15, 2012, now U.S. Pat. No. 8,932,591, issued Jan. 13, 2015, which is a continuation of U.S. patent application Ser. No. 10/525,292 filed Oct. 27, 2005, now U.S. Pat. No. 8,216,583, issued Jul. 10, 2012, which is a United States National Stage Application under 35 U.S.C. § 371 of PCT/IB2003/004502, filed Aug. 15, 2003 (now expired), which is a continuation of U.S. patent application Ser. No. 10/222,140, filed Aug. 16, 2002 (now abandoned). Each of these applications is herein incorporated by reference in its entirety.

SEQUENCE LISTING

The Sequence Listing associated with this application is provided in text format in lieu of a paper copy, and is hereby incorporated by reference into the specification. The name of the text file containing the Sequence Listing is 110222-0005-319-SL.txt. The text file is 11,449 bytes in size, was created on Apr. 11, 2016, and is being submitted electronically via EFS Web.

BACKGROUND OF THE INVENTION

Tumor necrosis factor α (TNFα) is a cytokine produced by numerous cell types, including monocytes and macrophages, that was originally identified based on its capacity to induce the necrosis of certain mouse tumors (see e.g., Old, L. (1985) *Science* 230:630-632). Subsequently, a factor termed cachectin, associated with cachexia, was shown to be the same molecule as TNFα. TNFα has been implicated in mediating shock (see e.g., Beutler, B. and Cerami, A. (1988) *Annu. Rev. Biochem.* 57:505-518; Beutler, B. and Cerami, A. (1989) *Annu. Rev. Immunol.* 7:625-655). Furthermore, TNFα has been implicated in the pathophysiology of a variety of other human diseases and disorders, including sepsis, infections, autoimmune diseases, transplant rejection and graft-versus-host disease (see e.g., Moeller, A., et al. (1990) *Cytokine* 2:162-169; U.S. Pat. No. 5,231,024 to Moeller et al.; European Patent Publication No. 260 610 B1 by Moeller, A., et al. Vasilli, P. (1992) *Annu. Rev. Immunol.* 10:411-452; Tracey, K. J. and Cerami, A. (1994) *Annu. Rev. Med.* 45:491-503).

Because of the harmful role of human TNFα (hTNFα) in a variety of human disorders, therapeutic strategies have been designed to inhibit or counteract hTNFα activity. In particular, antibodies that bind to, and neutralize, hTNFα have been sought as a means to inhibit hTNFα activity. Some of the earliest of such antibodies were mouse monoclonal antibodies (mAbs), secreted by hybridomas prepared from lymphocytes of mice immunized with hTNFα (see e.g., Hahn T; et al., (1985) *Proc Natl Acad Sci USA* 82:3814-3818; Liang, C-M., et al. (1986) *Biochem. Biophys. Res. Commun.* 137:847-854; Hirai, M., et al. (1987) *J. Immunol. Methods* 96:57-62; Fendly, B. M., et al. (1987) *Hybridoma* 6:359-370; Moeller, A., et al. (1990) *Cytokine* 2:162-169; U.S. Pat. No. 5,231,024 to Moeller et al.; European Patent Publication No. 186 833 B1 by Wallach, D.; European Patent Application Publication No. 218 868 A1 by Old et al.; European Patent Publication No. 260 610 B1 by Moeller, A., et al.). While these mouse anti-hTNFα antibodies often displayed high affinity for hTNFα (e.g., $Kd \leq 10^{-9}M$) and were able to neutralize hTNFα activity, their use in vivo may be limited by problems associated with administration of mouse antibodies to humans, such as short serum half life, an inability to trigger certain human effector functions and elicitation of an unwanted immune response against the mouse antibody in a human (the "human anti-mouse antibody" (HAMA) reaction).

In an attempt to overcome the problems associated with use of fully-murine antibodies in humans, murine anti-hTNFα antibodies have been genetically engineered to be more "human-like." For example, chimeric antibodies, in which the variable regions of the antibody chains are murine-derived and the constant regions of the antibody chains are human-derived, have been prepared (Knight, D. M, et al. (1993) *Mol. Immunol.* 30:1443-1453; PCT Publication No. WO 92/16553 by Daddona, P. E., et al.). Additionally, humanized antibodies, in which the hypervariable domains of the antibody variable regions are murine-derived but the remainder of the variable regions and the antibody constant regions are human-derived, have also been prepared (PCT Publication No. WO 92/11383 by Adair, J. R., et al.). However, because these chimeric and humanized antibodies still retain some murine sequences, they still may elicit an unwanted immune reaction, the human anti-chimeric antibody (HACA) reaction, especially when administered for prolonged periods, e.g., for chronic indications, such as rheumatoid arthritis (see e.g., Elliott, M. J., et al. (1994) *Lancet* 344:1125-1127; Elliot, M. J., et al. (1994) *Lancet* 344:1105-1110).

A preferred hTNFα inhibitory agent to murine mAbs or derivatives thereof (e.g., chimeric or humanized antibodies) would be an entirely human anti-hTNFα antibody, since such an agent should not elicit the HAMA reaction, even if used for prolonged periods. Human monoclonal autoantibodies against hTNFα have been prepared using human hybridoma techniques (Boyle, P., et al. (1993) *Cell. Immunol.* 152:556-568; Boyle, P., et al. (1993) *Cell. Immunol.* 152:569-581; European Patent Application Publication No. 614 984 A2 by Boyle, et al.). However, these hybridoma-derived monoclonal autoantibodies were reported to have an affinity for hTNFα that was too low to calculate by conventional methods, were unable to bind soluble hTNFα and were unable to neutralize hTNFα-induced cytotoxicity (see Boyle, et al.; supra). Moreover, the success of the human hybridoma technique depends upon the natural presence in human peripheral blood of lymphocytes producing autoantibodies specific for hTNFα. Certain studies have detected serum autoantibodies against hTNFα in human subjects (Fomsgaard, A., et al. (1989) *Scand. J. Immunol.* 30:219-223; Bendtzen, K., et al. (1990) *Prog. Leukocyte Biol.* 10B:447-452), whereas others have not (Leusch, H-G., et al. (1991) *J. Immunol. Methods* 139:145-147).

Alternative to naturally-occurring human anti-hTNFα antibodies would be a recombinant hTNFα antibody. Recombinant human antibodies that bind hTNFα with relatively low affinity (i.e., $K_d \sim 10^{-7}$M) and a fast off rate (i.e., $K_{off} \sim 10^{-2}$ sec$^{-1}$) have been described (Griffiths, A D., et al. (1993) *EMBO* J. 12:725-734). However, because of their relatively fast dissociation kinetics, these antibodies may not be suitable for therapeutic use. Additionally, a recombinant human anti-hTNFα has been described that does not neutralize hTNFα activity, but rather enhances binding of hTNFα to the surface of cells and enhances internalization of hTNFα (Lidbury, A., et al. (1994) *Biotechnol. Ther.* 5:27-45; PCT Publication No. WO 92/03145 by Aston, R. et al.)

Recombinant human antibodies that bind soluble hTNFα with high affinity and slow dissociation kinetics and that have the capacity to neutralize hTNFα activity, including hTNFα-induced cytotoxicity (in vitro and in vivo) and hTNFα-induced cell activation, have also been described (see U.S. Pat. No. 6,090,382).

SUMMARY OF THE INVENTION

There is a need for a stable aqueous pharmaceutical formulation with an extended shelf life, comprising an antibody which is suitable for therapeutic use to inhibit or counteract detrimental hTNFα activity. There is also a need for a stable aqueous pharmaceutical formulation with an extended shelf life, comprising an antibody suitable for therapeutic use which is easily administered and contains a high protein concentration.

This invention provides a liquid aqueous pharmaceutical formulation consisting of a therapeutically effective amount of an antibody in a buffered solution forming a formulation having a pH between about 4 and about 8 and having a shelf life of at least 18 months. The invention also includes an aqueous pharmaceutical formulation comprising a therapeutically effective amount of an antibody in a buffered solution forming a formulation having a pH between about 4 and 8 and having a shelf life of at least 18 months in the liquid state. In one embodiment, the pharmaceutical formulation has enhanced stability. In a further embodiment, the formulation of the invention is stable following at least 3 freeze/thaw cycles of the formulation. In another embodiment, the antibody is directed to TNFα. In yet another embodiment, the antibody is directed to human TNFα. In still another embodiment, the antibody is D2E7.

This invention also provides a liquid aqueous pharmaceutical formulation comprising a therapeutically effective amount of an antibody in a buffered solution forming a formulation having a pH between 4 and 8 and having enhanced stability of at least 12 months at a temperature of 2-8° C. In one embodiment, the formulation has enhanced stability of at least 18 months. In another embodiment, the antibody is directed to TNFα. In yet another embodiment, the antibody is directed to human TNFα. In a further embodiment, the antibody is D2E7.

The invention further provides a liquid aqueous pharmaceutical formulation comprising a therapeutically effective amount of an antibody in a buffered solution forming a formulation having a pH between about 4 and about 8 which is easily administratable. In one embodiment, the antibody is directed to TNFα. In yet another embodiment, the antibody is directed to human TNFα. In a further embodiment, the antibody is D2E7.

In one embodiment of the invention, the liquid aqueous pharmaceutical formulation is suitable for injection. In a further embodiment, the formulation is suitable for single use sc injection. In another embodiment, the concentration of the antibody in the liquid aqueous pharmaceutical formulation is about 1-150 mg/ml. In yet another embodiment, the concentration of the antibody in the formulation is about 50 mg/ml. In still another embodiment, the formulation has a high protein concentration. In yet another embodiment of the invention, the formulation is not light sensitive.

In one embodiment of the invention, the liquid aqueous pharmaceutical formulation contains an antibody, or an antigen-binding portion thereof, that dissociates from human TNFα with a $K_d$ of $1 \times 10^{-8}$ M or less and a $K_{off}$ rate constant of $1 \times 10^{-3}$ s$^{-1}$ or less, both determined by surface plasmon resonance, and neutralizes human TNFα cytotoxicity in a standard in vitro L929 assay with an IC$_{50}$ of $1 \times 10^{-7}$ M or less. In another embodiment, the formulation of the invention contains an antibody, or antigen-binding portion thereof, which dissociates from human TNFα with a $K_{off}$ rate constant of $5 \times 10^{-4}$ s$^{-1}$ or less. In a further embodiment, the formulation contains an antibody, or antigen-binding portion thereof, which dissociates from human TNFα with a $K_{off}$ rate constant of $1 \times 10^{-4}$ s$^{-1}$ or less. In still a further embodiment, the formulation of the invention contains an antibody, or antigen-binding portion thereof, which neutralizes human TNFα cytotoxicity in a standard in vitro L929 assay with an IC$_{50}$ of $1 \times 10^{-8}$ M or less. In yet another embodiment of the invention, the claimed formulation includes an antibody, or antigen-binding portion thereof, which neutralizes human TNFα cytotoxicity in a standard in vitro L929 assay with an IC$_{50}$ of $1 \times 10^{-9}$ M or less. Another embodiment of the invention, includes a formulation where the antibody, or antigen-binding portion thereof, neutralizes human TNFα cytotoxicity in a standard in vitro L929 assay with an IC$_{50}$ of $1 \times 10^{-10}$ M or less.

In another embodiment of the invention, the liquid aqueous pharmaceutical formulation contains of an antibody, or antigen-binding portion thereof, which is a recombinant antibody, or antigen-binding portion thereof. In another embodiment, the formulation contains an antibody, or antigen-binding portion thereof, which inhibits human TNFα-induced expression of ELAM-1 on human umbilical vein endothelial cells. In still another embodiment, the claimed formulation includes the D2E7 antibody.

In another embodiment of the invention, the liquid aqueous pharmaceutical formulation includes an antibody, or antigen-binding portion, thereof which dissociates from human TNFα with a $K_{off}$ rate constant of $1 \times 10^{-3}$ s$^{-1}$ or less, as determined by surface plasmon resonance;

b) has a light chain CDR3 domain comprising the amino acid sequence of SEQ ID NO: 3, or modified from SEQ ID NO: 3 by a single alanine substitution at position 1, 4, 5, 7 or 8 or by one to five conservative amino acid substitutions at positions 1, 3, 4, 6, 7, 8 and/or 9;

c) has a heavy chain CDR3 domain comprising the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12. In another embodiment, the formulation of the invention includes an antibody, or an antigen-binding portion thereof, which dissociates from human TNFα with a $K_{off}$ rate constant of $5 \times 10^{-4}$ s$^{-1}$ or less. In yet another embodiment of the invention, the formulation includes an antibody, or an antigen-binding portion thereof, which dissociates from human TNFα with a $K_{off}$ rate constant of $1 \times 10^{-4}$ s$^{-1}$ or less.

In yet another embodiment of the invention, the liquid aqueous pharmaceutical formulation, contains of an antibody, or antigen-binding portion thereof, which has a light chain variable region (LCVR) having a CDR3 domain comprising the amino acid sequence of SEQ ID NO: 3, or modified from SEQ ID NO: 3 by a single alanine substitution at position 1, 4, 5, 7 or 8, and with a heavy chain variable region (HCVR) having a CDR3 domain comprising the amino acid sequence of SEQ ID NO: 4, or modified from SEQ ID NO: 4 by a single alanine substitution at position 2, 3, 4, 5, 6, 8, 9, 10 or 11. In a further embodiment, the formulation of the invention contains an antibody, wherein the LCVR of the antibody, or an antigen-binding portion thereof, further has a CDR2 domain comprising the amino acid sequence of SEQ ID NO: 5 and the HCVR of the antibody, or an antigen-binding portion thereof, further has a CDR2 domain comprising the amino acid sequence of SEQ ID NO: 6. In yet another embodiment, the formulation of the invention contains an antibody, wherein the LCVR of the antibody, or an antigen-binding portion thereof, further has CDR1 domain comprising the amino acid sequence of SEQ ID NO: 7 and the HCVR has a CDR1 domain comprising the amino acid sequence of SEQ ID NO: 8.

In yet another embodiment of the invention, the antibody or antigen-binding portion thereof, contained in the liquid aqueous pharmaceutical formulation has a light chain variable region (LCVR) comprising the amino acid sequence of SEQ ID NO: 1 and a heavy chain variable region (HCVR) comprising the amino acid sequence of SEQ ID NO: 2. In another embodiment, the antibody, or antigen-binding portion thereof, has an IgG1 heavy chain constant region. In still another embodiment, the antibody, or antigen-binding portion thereof, has an IgG4 heavy chain constant region. In another embodiment, the antibody, or antigen-binding portion thereof, is a Fab fragment. In still a further embodiment, the antibody, or antigen-binding portion thereof, is a single chain Fv fragment.

In one embodiment of the invention, the liquid aqueous pharmaceutical formulation, contains an antibody, or antigen-binding portion thereof, which has a light chain variable region (LCVR) having a CDR3 domain comprising an amino acid sequence selected from the group consisting of SEQ ID NO: 3, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26 or with a heavy chain variable region (HCVR) having a CDR3 domain comprising an amino acid sequence selected from the group consisting of SEQ ID NO: 4, SEQ ID NO: 27, SEQ ID NO: 28, SEQ ID NO: 29, SEQ ID NO: 30, SEQ ID NO: 31, SEQ ID NO: 32, SEQ ID NO: 33 and SEQ ID NO: 34. In still another embodiment, the antibody, or antigen-binding portion thereof, neutralizes the activity of human TNFα, chimpanzee TNFα and at least one additional primate TNFα selected from the group consisting of baboon TNFα, marmoset TNFα, cynomolgus TNFα and rhesus TNFα. In a further embodiment, the formulation of the invention includes an antibody, or an antigen-binding portion thereof, which also neutralizes the activity of mouse TNFα. The formulation of the invention also an antibody, or an antigen-binding portion thereof, which neutralizes the activity of pig TNFα.

In a further embodiment, the invention provides a liquid aqueous pharmaceutical formulation which contains an antibody, or antigen-binding portion thereof, which binds to human TNFα and comprises:

a light chain CDR3 domain comprising the amino acid sequence of SEQ ID NO: 3, or modified from SEQ ID NO: 3 by a single alanine substitution at position 1, 4, 5, 7 or 8 or by one to five conservative amino acid substitutions at positions 1, 3, 4, 6, 7, 8 and/or 9, and a heavy chain CDR3 domain comprising the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12. In one embodiment, the liquid aqueous pharmaceutical formulation includes an antibody which bind human TNFα and comprises a light chain variable region (LCVR) having a CDR3 domain comprising an amino acid sequence selected from the group consisting of SEQ ID NO: 3, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26 or a heavy chain variable region (HCVR) having a CDR3 domain comprising an amino acid sequence selected from the group consisting of SEQ ID NO: 4, SEQ ID NO: 27, SEQ ID NO: 28, SEQ ID NO: 29, SEQ ID NO: 30, SEQ ID NO: 31, SEQ ID NO: 32, SEQ ID NO: 33 and SEQ ID NO: 34. In a further embodiment of the invention, the antibody, or antigen-binding portion thereof, binds human TNFα and is the antibody D2E7 or an antigen binding portion thereof.

The invention also provides an aqueous pharmaceutical composition comprising a polyol, a surfactant, and a buffer system comprising citrate and/or phosphate with a pH of about 4 to 8, in amounts sufficient to formulate an antibody for therapeutic use at a concentration of greater than about 45 mg/ml. In one embodiment, the polyol is mannitol and the surfactant is polysorbate 80. In another embodiment, the composition includes 5-20 mg/ml of mannitol and 0.1-10 mg/ml of polysorbate 80. In a further embodiment, the composition includes the antibody D2E7.

The invention also provides a liquid aqueous pharmaceutical formulation consisting of 1-150 mg/ml of antibody, 5-20 mg/ml of mannitol, 0.1-10 mg/ml of Tween-80, and a buffer system comprising citrate and/or phosphate, with a pH of 4 to 8. In one embodiment, the antibody is directed to hTNFα. In another embodiment, the formulation contains about 40 mg of antibody. The invention further provides a liquid aqueous pharmaceutical formulation comprising about 50 mg/ml of antibody, about 12 mg/ml of mannitol, about 1 mg/ml of Tween-80, and a buffer system comprising citrate and/or phosphate, with a pH of about 4 to about 8. In one embodiment, the pH of the formulation is between about 4.5 to about 6.0. In another embodiment, the pH is between about 4.8 to about 5.5. In yet another embodiment, the pH of the invention is between about 5.0 to about 5.2.

In one embodiment of the invention, the liquid aqueous pharmaceutical formulation also includes about 1.305 mg/ml of citric acid, about 0.305 mg/ml of sodium citrate, about 1.53 mg/ml of disodium phosphate dihydrate, about 0.86 mg/ml of sodium dihydrogen phosphate dihydrate, and about 6.165 mg/ml of sodium chloride. In another embodiment, the formulation of the invention includes an antibody which is directed to hTNFα. In yet another embodiment, the formulation of the invention includes the antibody D2E7. In yet a further embodiment, the formulation of the invention is administered to a subject suffering from a disorder in which TNFα activity is detrimental such that TNFα activity in the subject is inhibited

DETAILED DESCRIPTION OF THE INVENTION

This invention pertains to a liquid aqueous pharmaceutical formulation with a pH of about 4 to about 8 which contains a high protein concentration, including an antibody concentration ranging from about 1 to about 150 mg/ml, and has enhanced stability. This invention also pertains to a liquid aqueous pharmaceutical formulation for therapeutic use in a subject suffering from a condition characterized by detrimental TNFα activity. The formulation of the invention comprises the following constituents: an antibody which binds to human TNFα with high affinity, a low off rate and high neutralizing capacity; a buffer, which includes citric acid, sodium citrate, disodium phosphate dihydrate, and sodium dihydrogen phosphate dihydrate; tonicity agents, which include mannitol and sodium chloride; a detergent, including polysorbate 80; and sodium hydroxide, for pH adjustment.

Definitions

In order that the present invention may be more readily understood, certain terms are first defined.

The term "subject" is intended to include living organisms, e.g., prokaryotes and eukaryotes. Examples of subjects include mammals, e.g., humans, dogs, cows, horses, pigs, sheep, goats, cats, mice, rabbits, rats, and transgenic non-human animals. In specific embodiments of the invention, the subject is a human.

The term "pharmaceutical formulation" refers to preparations which are in such form as to permit the biological activity of the active ingredients to be unequivocally effective, and which contain no additional components which are significantly toxic to the subjects to which the formulation would be administered. "Pharmaceutically acceptable" excipients (vehicles, additives) are those which can reasonably be administered to a subject mammal to provide an effective dose of the active ingredient employed.

A "stable" formulation is one in which the antibody therein essentially retains its physical stability and/or chemical stability and/or biological activity upon storage. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993), for example. Stability can be measured at a selected temperature for a selected time period. Preferably, the formulation is stable at room temperature (about 30° C.) or at 40° C. for at least 1 month and/or stable at about 2-8° C. for at least 1 year for at least 2 years. Furthermore, the formulation is preferably stable following freezing (to, e.g., −70° C.) and thawing of the formulation, hereinafter referred to as a "freeze/thaw cycle."

An antibody "retains its physical stability" in a pharmaceutical formulation if it shows substantially no signs of aggregation, precipitation and/or denaturation upon visual examination of color and/or clarity, or as measured by UV light scattering or by size exclusion chromatography.

An antibody "retains its chemical stability" in a pharmaceutical formulation, if the chemical stability at a given time is such that the antibody is considered to still retain its biological activity as defined below. Chemical stability can be assessed by detecting and quantifying chemically altered forms of the antibody. Chemical alteration may involve size modification (e.g. clipping) which can be evaluated using size exclusion chromatography, SDS-PAGE and/or matrix-assisted laser desorption ionization/time-of-flight mass spectrometry (MALDI/TOF MS), for example. Other types of chemical alteration include charge alteration (e.g. occurring as a result of deamidation) which can be evaluated by ion-exchange chromatography, for example.

An antibody "retains its biological activity" in a pharmaceutical formulation, if the antibody in a pharmaceutical formulation is biologically active for its intended purpose. For example, biological activity is retained if the biological activity of the antibody in the pharmaceutical formulation is within about 30%, about 20%, or about 10% (within the errors of the assay) of the biological activity exhibited at the time the pharmaceutical formulation was prepared (e.g., as determined in an antigen binding assay).

"Isotonic" is a term recognized in the art. Isotonic can mean, for example, that the formulation of interest has essentially the same osmotic pressure as human blood. Isotonic formulations will generally have an osmotic pressure from about 250 to 350 mOsm. Isotonicity can be measured using a vapor pressure or ice-freezing type osmometer, for example. A "tonicity agent" is a compound which renders the formulation isotonic.

A "polyol" is a substance with multiple hydroxyl groups, and includes sugars (reducing and nonreducing sugars), sugar alcohols and sugar acids. Preferred polyols herein have a molecular weight which is less than about 600 kD (e.g. in the range from about 120 to about 400 kD). A "reducing sugar" is one which contains a hemiacetal group that can reduce metal ions or react covalently with lysine and other amino groups in proteins and a "nonreducing sugar" is one which does not have these properties of a reducing sugar. Examples of reducing sugars are fructose, mannose, maltose, lactose, arabinose, xylose, ribose, rhamnose, galactose and glucose. Nonreducing sugars include sucrose, trehalose, sorbose, melezitose and raffinose. Mannitol, xylitol, erythritol, threitol, sorbitol and glycerol are examples of sugar alcohols. As to sugar acids, these include L-gluconate and metallic salts thereof. Where it desired that the formulation is freeze-thaw stable, the polyol is preferably one which does not crystallize at freezing temperatures (e.g. −20° C.) such that it destabilizes the antibody in the formulation. The polyl may also act as a tonicity agent. In one embodiment of the invention, one ingredient of the formulation is mannitol in a concentration of 5 to 20 mg/ml. In a preferred embodiment of the invention, the concentration of mannitol is 7.5 to 15 mg/ml. In a more preferred embodiment of the invention, the concentration of mannitol is 10-14 mg/ml.

As used herein, "buffer" refers to a buffered solution that resists changes in pH by the action of its acid-base conjugate components. The buffer of this invention has a pH in the range from about 4 to about 8; preferably from about 4.5 to about 7; and most preferably has a pH in the range from about 5.0 to about 6.5. Examples of buffers that will control the pH in this range include acetate (e.g. sodium acetate), succinate (such as sodium succinate), gluconate, histidine, citrate and other organic acid buffers.

In a pharmacological sense, in the context of the present invention, a "therapeutically effective amount" or "effective amount" of an antibody refers to an amount effective in the prevention or treatment of a disorder for the treatment of which the antibody is effective. A "disorder" is any condition that would benefit from treatment with the antibody. This includes chronic and acute disorders or diseases including those pathological conditions which predisposes the subject to the disorder in question.

A "preservative" is a compound which can be included in the formulation to essentially reduce bacterial action therein, thus facilitating the production of a multi-use formulation, for example. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol.

"Treatment" refers to both therapeutic treatment and prophylactic or preventative measures. Those in need of treatment include those already with the disorder as well as those in which the disorder is to be prevented.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

The phrase "pharmaceutically acceptable carrier" is art recognized and includes a pharmaceutically acceptable material, composition or vehicle, suitable for administration to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient.

The term "human TNFα" (abbreviated herein as hTNFα, or simply hTNF), as used herein, is intended to refer to a human cytokine that exists as a 17 kD secreted form and a 26 kD membrane associated form, the biologically active form of which is composed of a trimer of noncovalently bound 17 kD molecules. The structure of hTNFα is described further in, for example, Pennica, D., et al. (1984) *Nature* 312:724-729; Davis, J. M., et al. (1987) *Biochemistry* 26:1322-1326; and Jones, E. Y., et al. (1989) *Nature* 338: 225-228. The term human TNFα is intended to include recombinant human TNFα (rhTNFα), which can be prepared by standard recombinant expression methods or purchased commercially (R & D Systems, Catalog No. 210-TA, Minneapolis, Minn.).

The term "antibody", as used herein, is intended to refer to immunoglobulin molecules comprised of four polypeptide chains, two heavy (H) chains and two light (L) chains inter-connected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. In one embodiment of the invention, the formulation contains an antibody with CDR1, CDR2, and CDR3 sequences like those described in U.S. Pat. Nos. 6,090,382 and 6,258,562, each incorporated by reference herein.

The term "antigen-binding portion" of an antibody (or simply "antibody portion"), as used herein, refers to one or more fragments of an antibody that retain the ability to specifically bind to an antigen (e.g., hTNFα). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123). In one embodiment of the invention, the formulation contains an antigen-binding portions described in U.S. Pat. Nos. 6,090,382 and 6,258,562, each incorporated by reference herein.

Still further, an antibody or antigen-binding portion thereof may be part of a larger immunoadhesion molecules, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) *Human Antibodies and Hybridomas* 6:93-101) and use of a cysteine residue, a marker peptide and a C-terminal polyhistidine tag to make bivalent and biotinylated scFv molecules (Kipriyanov, S. M., et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

The term "human antibody", as used herein, is intended to include antibodies having variable and constant regions derived from human germline immunoglobulin sequences.

The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further in Section II, below), antibodies isolated from a recombinant, combinatorial human antibody library (described further in Section III, below), antibodies isolated from an animal (e.g., a mouse) that is transgenic for human immunoglobulin genes (see e.g., Taylor, L. D., et al. (1992) *Nucl. Acids Res.* 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

An "isolated antibody", as used herein, is intended to refer to an antibody that is substantially free of other antibodies having different antigenic specificities (e.g., an isolated antibody that specifically binds hTNFα is substantially free of antibodies that specifically bind antigens other than hTNFα). An isolated antibody that specifically binds hTNFα may, however, have cross-reactivity to other antigens, such as TNFα molecules from other species. Moreover, an isolated antibody may be substantially free of other cellular material and/or chemicals.

A "neutralizing antibody", as used herein (or an "antibody that neutralized hTNFα activity"), is intended to refer to an antibody whose binding to hTNFα results in inhibition of the biological activity of hTNFα. This inhibition of the biological activity of hTNFα can be assessed by measuring one or more indicators of hTNFα biological activity, such as hTNFα-induced cytotoxicity (either in vitro or in vivo), hTNFα-induced cellular activation and hTNFα binding to hTNFα receptors. These indicators of hTNFα biological activity can be assessed by one or more of several standard in vitro or in vivo assays known in the art, and described in U.S. Pat. Nos. 6,090,382 and 6,258,562, each incorporated by reference herein. Preferably, the ability of an antibody to neutralize hTNFα activity is assessed by inhibition of hTNFα-induced cytotoxicity of L929 cells. As an additional or alternative parameter of hTNFα activity, the ability of an antibody to inhibit hTNFα-induced expression of ELAM-1 on HUVEC, as a measure of hTNFα-induced cellular activation, can be assessed.

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Jönsson, U., et al. (1993) *Ann. Biol. Clin.* 51:19-26; Jönsson, U., et al. (1991) *Biotechniques* 11:620-627; Johnsson, B., et al. (1995) *J. Mol. Recognit.* 8:125-131; and Johnnson, B., et al. (1991) *Anal. Biochem.* 198:268-277.

The term "$K_{off}$", as used herein, is intended to refer to the off rate constant for dissociation of an antibody from the antibody/antigen complex.

The term "$K_d$", as used herein, is intended to refer to the dissociation constant of a particular antibody-antigen interaction.

II. Antibodies of the Formulation

The invention is directed to a liquid aqueous pharmaceutical formulation comprising a therapeutically effective amount of an antibody in a buffered solution forming a formulation having a pH between about 4 and about 8 and having an extended shelf life, preferably of at least about 18 months. In another embodiment, the liquid aqueous pharmaceutical formulation of the invention has enhanced stability. In a further embodiment of the invention, the formulation is not light sensitive. In yet another embodiment of the invention, the claimed formulation remains stable following at least 3 freeze/thaw cycles. In still another embodiment, the pharmaceutical formulation of the invention is suitable for single use sc injection.

Antibodies that can be used in the formulation include polyclonal, monoclonal, recombinant antibodies, single chain antibodies, hybrid antibodies, chimeric antibodies, humanized antibodies, or fragments thereof. Antibody-like molecules containing one or two binding sites for an antigen and a Fc-part of an immunoglobulin can also be used. An example of an antibody-like molecule is the active ingredient etanercept or infliximab. Preferred antibodies used in the formulation are human antibodies which are cloned from human cells or from gene-archives representing the human antibody-reservoir. Especially preferred among the human antibodies are antibodies directed against the antigen TNFα, including human TNFα (or hTNFα).

In one embodiment, the formulation of the invention includes a combination of antibodies (two or more), or a "cocktail" of antibodies. For example, the formulation can include the antibody D2E7 and one or more additional antibodies.

In a preferred embodiment of the invention, the formulation contains an antibody, or antigen-binding portion thereof, dissociates from human TNFα with a $K_d$ of $1\times10^{-8}$ M or less and a $K_{off}$ rate constant of $1\times10^{-3}$ s$^{-1}$ or less, both determined by surface plasmon resonance, and neutralizes human TNFα cytotoxicity in a standard in vitro L929 assay with an IC$_{50}$ of $1\times10^{-7}$ M or less. In another preferred embodiment, the formulation of the invention contains an antibody, or antigen-binding portion thereof, like those described in U.S. Pat. Nos. 6,090,382 and 6,258,562, each incorporated by reference herein.

In one aspect, the formulation of the invention contains D2E7 antibodies and antibody portions, D2E7-related antibodies and antibody portions, and other human antibodies and antibody portions with equivalent properties to D2E7, such as high affinity binding to hTNFα with low dissociation kinetics and high neutralizing capacity. In another one embodiment, the formulation of the invention contains an isolated human antibody, or an antigen-binding portion thereof, that dissociates from human TNFα with a $K_d$ of $1\times10^{-8}$ M or less and a $K_{off}$ rate constant of $1\times10^{-3}$ s$^{-1}$ or less, both determined by surface plasmon resonance, and neutralizes human TNFα cytotoxicity in a standard in vitro L929 assay with an $IC_{50}$ of $1\times10^{-7}$ M or less. More preferably, the isolated human antibody, or antigen-binding portion thereof, dissociates from human TNFα with a $K_{off}$ of $5\times10^{-4}$ $s^{-1}$ or less, or even more preferably, with a $K_{off}$ of $1\times10^{-4}$ $s^{-1}$ or less. More preferably, the isolated human antibody, or antigen-binding portion thereof, neutralizes human TNFα cytotoxicity in a standard in vitro L929 assay with an $IC_{50}$ of $1\times10^{-8}$ M or less, even more preferably with an $IC_{50}$ of $1\times10^{-9}$ M or less and still more preferably with an $IC_{50}$ of $5\times10^{-10}$ M or less. In a preferred embodiment, the formulation contains an antibody which is an isolated human recombinant antibody, or an antigen-binding portion thereof. In another preferred embodiment, the formulation contains an antibody which also neutralizes TNFα-induced cellular activation, as assessed using a standard in vitro assay for TNFα-induced ELAM-1 expression on human umbilical vein endothelial cells (HUVEC).

III. Preparation of Formulation

The present invention features formulations (e.g., protein formulations and/or antibody formulations) having improved properties as compared to art-recognized formulations. For example, the formulations of the invention have an improved shelf life and/or stability as compared to art recognized formulations. In a preferred aspect, the formulations of the invention comprise a high protein concentration, including, for example, a protein concentration greater than about 45 mg/ml, a protein concentration greater than about 50 mg/ml, a protein concentration greater than about 100 mg/ml, or a protein concentration greater than about 150 mg/ml. In a preferred embodiment of the invention, the protein is an antibody. In another preferred embodiment, the antibody is D2E7. The invention also provides an aqueous pharmaceutical composition comprising a polyol, a surfactant, and a buffer system comprising citrate and/or phosphate with a pH of about 4 to 8, in amounts sufficient to formulate an antibody for therapeutic use at a concentration of greater than about, for example, 45 mg/ml.

Preparation of the antibody of interest is performed according to standard methods known in the art. In a preferred embodiment of the invention, the antibody used in the formulation is expressed in CHO cells and purified by a standard series of chromatography steps. In a further preferred embodiment, the antibody is directed to hTNFα, and is prepared according to the methods described in U.S. Pat. Nos. 6,090,382 and 6,258,562, each incorporated by reference herein.

After preparation of the antibody of interest, the pharmaceutical formulation comprising the antibody is prepared. The therapeutically effective amount of antibody present in the formulation is determined, for example, by taking into account the desired dose volumes and mode(s) of administration. In one embodiment of the invention, the concentration of the antibody in the formulation is between about 1 to about 150 mg of antibody per ml of liquid formulation. In a preferred embodiment, the concentration of the antibody in the formulation is between about 5 to about 80 mg per ml. In another preferred embodiment, the concentration of the antibody in the formulation is between about 25 to about 50 mg/ml. The formulation is especially suitable for large antibody dosages of more than 15 mg/ml. In a preferred embodiment, the concentration of the antibody is 50 mg/ml.

In another embodiment of the invention, the concentration of the antibody in the formulation is about 1-150 mg/ml, about 5-145 mg/ml, about 10-140 mg/ml, about 15-135 mg/ml, about 20-130 mg/ml, about 25-125 mg/ml, about 30-120 mg/ml, about 35-115 mg/ml, about 40-110 mg/ml, about 45-105 mg/ml, about 50-100 mg/ml, about 55-95 mg/ml, about 60-90 mg/ml, about 65-85 mg/ml, about 70-80 mg/ml, or about 75 mg/ml. Ranges intermediate to the above recited concentrations, e.g., about 6-144 mg/ml, are also intended to be part of this invention. For example, ranges of values using a combination of any of the above recited values as upper and/or lower limits are intended to be included.

In one embodiment, the invention provides a formulation with an extended shelf life comprising of an active ingredient, preferably an antibody, in combination with mannitol, citric acid monohydrate, sodium citrate, disodium phosphate dihydrate, sodium dihydrogen phosphate dihydrate, sodium chloride, polysorbate 80, water, and sodium hydroxide. In a further embodiment, the formulation of the invention has an extended shelf life of at least about 18 months in the liquid state. Freezing the formulation of the invention can also be used to further extend its shelf life.

An aqueous formulation is prepared comprising the antibody in a pH-buffered solution. The buffer of this invention has a pH ranging from about 4 to about 8, preferably from about 4.5 to about 6.0, more preferably from about 4.8 to about 5.5, and most preferably has a pH of about 5.0 to about 5.2. Ranges intermediate to the above recited pH's are also intended to be part of this invention. For example, ranges of values using a combination of any of the above recited values as upper and/or lower limits are intended to be included. Examples of buffers that will control the pH within this range include acetate (e.g. sodium acetate), succinate (such as sodium succinate), gluconate, histidine, citrate and other organic acid buffers.

In a preferred embodiment of the invention, the formulation comprises a buffer system which contains citrate and phosphate to maintain the pH in a range of about 4 to about 8. In a further preferred embodiment the pH range is from about 4.5 to about 6.0, more preferably from about pH 4.8 to about 5.5, and most preferably in a pH range of about 5.0 to about 5.2. In another preferred embodiment, the buffer system includes citric acid monohydrate, sodium citrate, disodium phosphate dihydrate, and/or sodium dihydrogen phosphate dihydrate. In a further preferred embodiment, the buffer system includes about 1.3 mg/ml of citric acid (e.g., 1.305 mg/ml), about 0.3 mg/ml of sodium citrate (e.g., 0.305 mg/ml), about 1.5 mg/ml of disodium phosphate dihydrate (e.g. 1.53 mg/ml), about 0.9 mg/ml of sodium dihydrogen phosphate dihydrate (e.g., 0.86), and about 6.2 mg/ml of sodium chloride (e.g., 6.165 mg/ml). In additional preferred embodiments, the buffer system includes 1-1.5 mg/ml of citric acid, 0.25 to 0.5 mg/ml of sodium citrate, 1.25 to 1.75 mg/ml of disodium phosphate dihydrate, 0.7 to 1.1 mg/ml of sodium dihydrogen phosphate dihydrate, and 6.0 to 6.4 mg/ml of sodium chloride. In a further embodiment, the pH of the formulation is adjusted with sodium hydroxide.

A polyol, which acts as a tonicifier and may stabilize the antibody, is also included in the formulation. The polyol is added to the formulation in an amount which may vary with respect to the desired isotonicity of the formulation. Preferably the aqueous formulation is isotonic. The amount of polyol added may also alter with respect to the molecular weight of the polyol. For example, a lower amount of a monosaccharide (e.g. mannitol) may be added, compared to a disaccharide (such as trehalose). In a preferred embodiment of the invention, the polyol which is used in the formulation as a tonicity agent is mannitol. In a preferred embodiment of the invention, the mannitol concentration is about 5 to 20 mg/ml. In another preferred embodiment of the invention, the concentration of mannitol is about 7.5 to 15 mg/ml. In a more preferred embodiment of the formulation of the invention, the concentration of mannitol is about 10-14 mg/ml. In the most preferred embodiment, the concentration of mannitol is about 12 mg/ml. In another embodiment of the invention, the polyol sorbitol is included in the formulation.

A detergent or surfactant is also added to the antibody formulation. Exemplary detergents include nonionic detergents such as polysorbates (e.g. polysorbates 20, 80 etc) or poloxamers (e.g. poloxamer 188). The amount of detergent added is such that it reduces aggregation of the formulated antibody and/or minimizes the formation of particulates in the formulation and/or reduces adsorption. In a preferred embodiment of the invention, the formulation includes a surfactant which is a polysorbate. In another preferred embodiment of the invention, the formulation contains the detergent polysorbate 80 or Tween 80. Tween 80 is a term used to describe polyoxyethylene (20) sorbitanmonooleate (see Fiedler, Lexikon der Hifsstoffe, Editio Cantor Verlag Aulendorf, 4th edi., 1996). In one preferred embodiment, the formulation contains between about 0.1 and about 10 mg/ml of polysorbate 80, more preferably between about 0.5 and about 5 mg/ml. In another preferred embodiment, about 0.1% polysorbate 80 is found in the formulation of the invention.

In a preferred embodiment of the invention, the formulation is a 0.8 mL solution in a vial containing the ingredients shown below in Table 1.

TABLE 1

1 vial with 0.8 mL solution for injection[1] contains:

| Name of ingredient | Quantity | Function |
|---|---|---|
| Active substance: | | |
| Antibody (D2E7)[2] | 40.0 mg | Active substance |
| Excipients: | | |
| Mannitol | 9.6 mg | Tonicity agent |
| Citric acid monohydrate | 1.044 mg | Buffer |
| Citric acid | | |
| Sodium citrate | 0.244 mg | Buffer |
| Sodium citrate | | |
| Disodium phosphate dihydrate | 1.224 mg | Buffer |
| Dibasic sodium phosphate dihydrate | | |
| Sodium dihydrogen phosphate dihydrate | 0.688 mg | Buffer |
| Monobasic sodium phosphate dihydrate | | |
| Sodium chloride | 4.932 mg | Tonicity agent |
| Polysorbate 80 | 0.8 mg | Detergent |
| Water for injections | 759.028-759.048 mg | Solvent |
| Water for injection | | |
| Sodium hydroxide[3] | 0.02-0.04 mg | pH adjustment |
| Total | 817.6 mg | |

[1] Density of the solution: 1.022 g/mL
[2] Is used as concentrate
[3] Addition as 1M solution In one embodiment, the formulation contains the above-identified agents (i.e. antibody, buffer, polyol and detergent) and is essentially free of one or more preservatives, such as benzyl alcohol, phenol, m-cresol, chlorobutanol and benzethonium Cl. In another embodiment, a preservative may be included in the formulation, particularly where the formulation is a multidose formulation. One or more other pharmaceutically acceptable carriers, excipients or stabilizers such as those described in Remington's Pharmaceutical Sciences 16th edition, Osol, A. Ed. (1980) may be included in the formulation provided that they do not significantly adversely affect the desired characteristics of the formulation. Acceptable carriers, excipients or stabilizers are non-toxic to recipients at the dosages and concentrations employed and include; additional buffering agents; co-solvents; antioxidants including ascorbic acid and methionine; chelating agents such as EDTA; metal complexes (e.g. Zn-protein complexes); biodegradable polymers such as polyesters; and/or salt-forming counterions such as sodium.

The formulation herein may also be combined with one or more other therapeutic agents as necessary for the particular indication being treated, preferably those with complementary activities that do not adversely affect the antibody of the formulation. Such therapeutic agents are suitably present in combination in amounts that are effective for the purpose intended. Additional therapeutic agents which can be combined with the formulation of the invention are further described in U.S. Pat. Nos. 6,090,382 and 6,258,562, each of which is incorporated herein by reference.

The formulations to be used for in vivo administration must be sterile. This is readily accomplished by filtration through sterile filtration membranes, prior to, or following, preparation of the formulation.

IV. Administration of Formulation

The formulation of the invention can be used in similar indications as those described in U.S. Pat. Nos. 6,090,382 and 6,258,562, each incorporated by reference herein, and further detailed below.

The language "effective amount" of the formulation is that amount necessary or sufficient to inhibit TNFα activity, e.g., prevent the various morphological and somatic symptoms of a detrimental TNFα activity-associated state. In another embodiment, the effective amount of the formulation is the amount necessary to achieve the desired result. In one example, an effective amount of the formulation is the amount sufficient to inhibit detrimental TNFα activity. In another example, an effective amount of the formulation is 0.8 mL of the formulation containing 40 mg of antibody, as described in table 1. The effective amount can vary depending on such factors as the size and weight of the subject, or the type of illness. For example, the choice of a TNFα activity-inhibiting formulation can affect what constitutes an "effective amount". One of ordinary skill in the art would be able to study the aforementioned factors and make the determination regarding the effective amount of the TNFα activity inhibiting formulation without undue experimentation.

The regimen of administration can affect what constitutes an effective amount. The TNFα activity-inhibiting formulation can be administered to the subject either prior to or after the onset of detrimental TNFα activity. Further, several divided dosages, as well as staggered dosages, can be administered daily or sequentially, or the dose can be continuously infused, or can be a bolus injection. Further, the dosages of the TNFα activity-inhibiting formulation can be proportionally increased or decreased as indicated by the exigencies of the therapeutic or prophylactic situation.

The term "treated," "treating" or "treatment" includes the diminishment or alleviation of at least one symptom associated or caused by the state, disorder or disease being treated. For example, treatment can be diminishment of one or several symptoms of a disorder or complete eradication of a disorder.

Actual dosage levels of the active ingredients (antibody) in the pharmaceutical formulation of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the antibody found in the formulation, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition of the present invention required. For example, the physician or veterinarian could start doses of the compounds of the pharmaceutical formulation at levels lower than that required in order to achieve the desired therapeutic effect and gradually increase the dosage until the desired effect is achieved.

In general, a suitable daily dose of a formulation of the invention will be that amount of the formulation that is the lowest dose effective to produce a therapeutic effect. Such an effective dose will generally depend upon the factors described above. An effective amount of the formulation of the present invention is an amount that inhibits TNFα activity in a subject suffering from a disorder in which TNFα activity is detrimental. In a preferred embodiment, the formulation provides an effective dose of 40 mg per injection of the active ingredient, the antibody. In another embodiment, the formulation provides an effective dose which ranges from about 1 to 150 mg of antibody. If desired, the effective daily dose of the pharmaceutical formulation may be administered as two, three, four, five, six or more sub-doses administered separately at appropriate intervals throughout the day, optionally, in unit dosage forms.

In one embodiment of the invention, the dosage of the antibody in the formulation is between about 5 to about 80 mg. In another embodiment, the dosage of the antibody in the formulation is between about 25 to about 50 mg. The formulation is especially suitable for large antibody dosages of more than 15 mg. In a preferred embodiment of the invention, the formulation provides an antibody at a dose of about 40 mg. In another preferred embodiment, the antibody is directed to TNFα. In the most preferred embodiment, the antibody is D2E7.

In one embodiment of the invention, the dosage of the antibody in the formulation is between about 1-150 mg, about 5-145 mg, about 10-140 mg, about 15-135 mg, about 20-130 mg, about 25-125 mg, about 30-120 mg, about 35-115 mg, about 40-110 mg, about 45-105 mg, about 50-100 mg, about 55-95 mg, about 60-90 mg, about 65-85 mg, about 70-80 mg, or about 75 mg. In a preferred embodiment, the dosage of the antibody is 40 mg. In a further preferred embodiment, the antibody is directed to TNFα. In the most preferred embodiment, the antibody is D2E7. Ranges intermediate to the above recited dosages, e.g., about 2-149 mg, are also intended to be part of this invention. For example, ranges of values using a combination of any of the above recited values as upper and/or lower limits are intended to be included.

It is to be noted that dosage values may vary with the severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The invention provides a pharmaceutical formulation with an extended shelf life, which, in one embodiment, is used to inhibit TNFα activity in a subject suffering from a disorder in which TNFα activity is detrimental, comprising administering to the subject an antibody or antibody portion of the invention such that TNFα activity in the subject is inhibited. Preferably, the TNFα is human TNFα and the subject is a human subject. Alternatively, the subject can be a mammal expressing a TNFα with which an antibody of the invention cross-reacts. Still further the subject can be a mammal into which has been introduced hTNFα (e.g., by administration of hTNFα or by expression of an hTNFα transgene). A formulation of the invention can be administered to a human subject for therapeutic purposes (discussed further below). In one embodiment of the invention, the liquid pharmaceutical formulation is easily administratable, which includes, for example, a formulation which is self-administered by the patient. In a preferred embodiment, the formulation of the invention is administered through sc injection, preferably single use. Moreover, a formulation of the invention can be administered to a non-human mammal expressing a TNFα with which the antibody cross-reacts (e.g., a primate, pig or mouse) for veterinary purposes or as an animal model of human disease. Regarding the latter, such animal models may be useful for evaluating the therapeutic efficacy of antibodies of the invention (e.g., testing of dosages and time courses of administration).

As used herein, the term "a disorder in which TNFα activity is detrimental" is intended to include diseases and other disorders in which the presence of TNFα in a subject suffering from the disorder has been shown to be or is suspected of being either responsible for the pathophysiology of the disorder or a factor that contributes to a worsening of the disorder. Accordingly, a disorder in which TNFα activity is detrimental is a disorder in which inhibition of TNFα activity is expected to alleviate the symptoms and/or progression of the disorder. Such disorders may be evidenced, for example, by an increase in the concentration of TNFα in a biological fluid of a subject suffering from the disorder (e.g., an increase in the concentration of TNFα in serum, plasma, synovial fluid, etc. of the subject), which can be detected, for example, using an anti-TNFα antibody as described above.

There are numerous examples of disorders in which TNFα activity is detrimental. Examples of disorders in which TNFα activity is detrimental are described in U.S. Application No. 60/397,275, incorporated by reference herein. Examples in which TNFα activity is detrimental are also described in U.S. Pat. Nos. 6,015,557, 6,177,077, 6,379,666, 6,419,934, 6,419,944, 6,423,321, and 6,428,787; U.S. Patent Application Nos. US2001/0016195, US2001/0004456, and US2001/026801; WO 00/50079 and WO 01/49321, each incorporated by reference herein.

The use of the antibodies and antibody portions of the invention in the treatment of specific disorders is discussed further below:

A. Sepsis

Tumor necrosis factor has an established role in the pathophysiology of sepsis, with biological effects that include hypotension, myocardial suppression, vascular leakage syndrome, organ necrosis, stimulation of the release of toxic secondary mediators and activation of the clotting cascade (see e.g., Tracey, K. J. and Cerami, A. (1994) *Annu. Rev. Med.* 45:491-503; Russell, D and Thompson, R. C. (1993) *Curr. Opin. Biotech.* 4:714-721). Accordingly, the formulation of the invention can be used to treat sepsis in any of its clinical settings, including septic shock, endotoxic shock, gram negative sepsis and toxic shock syndrome.

Furthermore, to treat sepsis, the formulation of the invention can be coadministered with one or more additional therapeutic agents that may further alleviate sepsis, such as an interleukin-1 inhibitor (such as those described in PCT Publication Nos. WO 92/16221 and WO 92/17583), the cytokine interleukin-6 (see e.g., PCT Publication No. WO 93/11793) or an antagonist of platelet activating factor (see e.g., European Patent Application Publication No. EP 374 510).

Additionally, in a preferred embodiment, the formulation of the invention is administered to a human subject within a subgroup of sepsis patients having a serum or plasma concentration of IL-6 above 500 pg/ml, and more preferably 1000 pg/ml, at the time of treatment (see PCT Publication No. WO 95/20978 by Daum, L., et al.).

B. Autoimmune Diseases

Tumor necrosis factor has been implicated in playing a role in the pathophysiology of a variety of autoimmune diseases. For example, TNFα has been implicated in activating tissue inflammation and causing joint destruction in rheumatoid arthritis (see e.g., Tracey and Cerami, supra; Arend, W. P. and Dayer, J-M. (1995) *Arth. Rheum.* 38:151-160; Fava, R. A., et al. (1993) *Clin. Exp. Immunol.* 94:261-266). TNFα also has been implicated in promoting the death of islet cells and in mediating insulin resistance in diabetes (see e.g., Tracey and Cerami, supra; PCT Publication No. WO 94/08609). TNFα also has been implicated in mediating cytotoxicity to oligodendrocytes and induction of inflammatory plaques in multiple sclerosis (see e.g., Tracey and Cerami, supra). Chimeric and humanized murine anti-hTNFα antibodies have undergone clinical testing for treatment of rheumatoid arthritis (see e.g., Elliott, M. J., et al. (1994) *Lancet* 344:1125-1127; Elliot, M. J., et al. (1994) *Lancet* 344:1105-1110; Rankin, E. C., et al. (1995) *Br. J. Rheumatol.* 34:334-342).

The formulation of the invention can be used to treat autoimmune diseases, in particular those associated with inflammation, including rheumatoid arthritis, rheumatoid spondylitis, osteoarthritis and gouty arthritis, allergy, multiple sclerosis, autoimmune diabetes, autoimmune uveitis and nephrotic syndrome. Typically, the formulation is administered systemically, although for certain disorders, local administration of the antibody or antibody portion at a site of inflammation may be beneficial (e.g., local administration in the joints in rheumatoid arthritis or topical application to diabetic ulcers, alone or in combination with a cyclohexane-ylidene derivative as described in PCT Publication No. WO 93/19751).

C. Infectious Diseases

Tumor necrosis factor has been implicated in mediating biological effects observed in a variety of infectious diseases. For example, TNFα has been implicated in mediating brain inflammation and capillary thrombosis and infarction in malaria (see e.g., Tracey and Cerami, supra). TNFα also has been implicated in mediating brain inflammation, inducing breakdown of the blood-brain barrier, triggering septic shock syndrome and activating venous infarction in meningitis (see e.g., Tracey and Cerami, supra). TNFα also has been implicated in inducing cachexia, stimulating viral proliferation and mediating central nervous system injury in acquired immune deficiency syndrome (AIDS) (see e.g., Tracey and Cerami, supra). Accordingly, the antibodies, and antibody portions, of the invention, can be used in the treatment of infectious diseases, including bacterial meningitis (see e.g., European Patent Application Publication No. EP 585 705), cerebral malaria, AIDS and AIDS-related complex (ARC) (see e.g., European Patent Application Publication No. EP 230 574), as well as cytomegalovirus infection secondary to transplantation (see e.g., Fietze, E., et al. (1994) *Transplantation* 58:675-680). The formulation of the invention, also can be used to alleviate symptoms associated with infectious diseases, including fever and myalgias due to infection (such as influenza) and cachexia secondary to infection (e.g., secondary to AIDS or ARC).

D. Transplantation

Tumor necrosis factor has been implicated as a key mediator of allograft rejection and graft versus host disease (GVHD) and in mediating an adverse reaction that has been observed when the rat antibody OKT3, directed against the T cell receptor CD3 complex, is used to inhibit rejection of renal transplants (see e.g., Tracey and Cerami, supra; Eason, J. D., et al. (1995) *Transplantation* 59:300-305; Suthanthiran, M. and Strom, T. B. (1994) *New Engl. J. Med.* 331:365-375). Accordingly, the formulation of the invention, can be used to inhibit transplant rejection, including rejections of allografts and xenografts and to inhibit GVHD. Although the antibody or antibody portion may be used alone, more preferably it is used in combination with one or more other agents that inhibit the immune response against the allograft or inhibit GVHD. For example, in one embodiment, the formulation of the invention is used in combination with OKT3 to inhibit OKT3-induced reactions. In another embodiment, the formulation of the invention is used in combination with one or more antibodies directed at other targets involved in regulating immune responses, such as the cell surface molecules CD25 (interleukin-2 receptor-α), CD11a (LFA-1), CD54 (ICAM-1), CD4, CD45, CD28/CTLA4, CD80 (B7-1) and/or CD86 (B7-2). In yet another embodiment, the formulation of the invention is used in combination with one or more general immunosuppressive agents, such as cyclosporin A or FK506.

E. Malignancy

Tumor necrosis factor has been implicated in inducing cachexia, stimulating tumor growth, enhancing metastatic potential and mediating cytotoxicity in malignancies (see e.g., Tracey and Cerami, supra). Accordingly, the formulation of the invention, can be used in the treatment of malignancies, to inhibit tumor growth or metastasis and/or to alleviate cachexia secondary to malignancy. The formulation may be administered systemically or locally to the tumor site.

F. Pulmonary Disorders

Tumor necrosis factor has been implicated in the pathophysiology of adult respiratory distress syndrome, including stimulating leukocyte-endothelial activation, directing cytotoxicity to pneumocytes and inducing vascular leakage syndrome (see e.g., Tracey and Cerami, supra). Accordingly, the formulation of the invention, can be used to treat various pulmonary disorders, including adult respiratory distress syndrome (see e.g., PCT Publication No. WO 91/04054), shock lung, chronic pulmonary inflammatory disease, pulmonary sarcoidosis, pulmonary fibrosis and silicosis. The formulation may be administered systemically or locally to the lung surface, for example as an aerosol.

G. Intestinal Disorders

Tumor necrosis factor has been implicated in the pathophysiology of inflammatory bowel disorders (see e.g., Tracy, K. J., et al. (1986) *Science* 234:470-474; Sun, X-M., et al. (1988) *J. Clin. Invest.* 81:1328-1331; MacDonald, T. T., et al. (1990) *Clin. Exp. Immunol.* 81:301-305). Chimeric murine anti-hTNFα antibodies have undergone clinical testing for treatment of Crohn's disease (van Dullemen, H. M., et al. (1995) *Gastroenterology* 109:129-135). The formulation of the invention, also can be used to treat intestinal disorders, such as idiopathic inflammatory bowel disease, which includes two syndromes, Crohn's disease and ulcerative colitis.

H. Cardiac Disorders

The formulation of the invention, also can be used to treat various cardiac disorders, including ischemia of the heart (see e.g., European Patent Application Publication No. EP 453 898) and heart insufficiency (weakness of the heart muscle)(see e.g., PCT Publication No. WO 94/20139).

I. Others

The pharmaceutical formulation of the invention, also can be used to treat various other disorders in which TNFα activity is detrimental. Examples of other diseases and disorders in which TNFα activity has been implicated in the pathophysiology, and thus which can be treated using the formulation of the invention, include inflammatory bone disorders and bone resorption disease (see e.g., Bertolini, D. R., et al. (1986) *Nature* 319:516-518; Konig, A., et al. (1988) *J. Bone Miner. Res.* 3:621-627; Lerner, U. H. and Ohlin, A. (1993) *J. Bone Miner. Res.* 8:147-155; and Shankar, G. and Stem, P. H. (1993) *Bone* 14:871-876), hepatitis, including alcoholic hepatitis (see e.g., McClain, C. J. and Cohen, D. A. (1989) *Hepatology* 9:349-351; Felver, M. E., et al. (1990) *Alcohol. Clin. Exp. Res.* 14:255-259; and Hansen, J., et al. (1994) *Hepatology* 20:461-474) and viral hepatitis (Sheron, N., et al. (1991) *J. Hepatol.* 12:241-245; and Hussain, M. J., et al. (1994) *J. Clin. Pathol.* 47:1112-1115), coagulation disturbances (see e.g., van der Poll, T., et al. (1990) *N. Engl. J. Med.* 322:1622-1627; and van der Poll, T., et al. (1991) *Prog. Clin. Biol. Res.* 367:55-60), burns (see e.g., Giroir, B. P., et al. (1994) *Am. J. Physiol.* 267:H118-124; and Liu, X. S., et al. (1994) *Burns* 20:40-44), reperfusion injury (see e.g., Scales, W. E., et al. (1994) *Am. J. Physiol.* 267:G1122-1127; Serrick, C., et al. (1994) *Transplantation* 58:1158-1162; and Yao, Y. M., et al. (1995) *Resuscitation* 29:157-168), keloid formation (see e.g., McCauley, R. L., et al. (1992) *J. Clin. Immunol.* 12:300-308), scar tissue formation; pyrexia; periodontal disease; obesity and radiation toxicity.

Other disorders in which TNFα activity is detrimental include, but are not limited to, adult Still's disease, Alzheimer's disease, ankylosing spondylitis, asthma, cancer and cachexia, atherosclerosis, chronic atherosclerosis, chronic fatigue syndrome, liver failure, chronic liver failure, obstructive pulmonary disease, chronic obstructive pulmonary disease, congestive heart failure, dermatopolymyositis, diabetic macrovasculopathy, endometriosis, familial periodic fevers, fibrosis, hemodialysis, Jarisch-Herxheimer reaction, juvenile RA, Kawasaki syndrome, myelo dysplastic syndrome, myocardial infarction, panciaticular vulgaris, periodontal disease, peripheral neuropathy, polyarticular, polymyositis, progressive renal failure, psoriasis, psoriatic arthritis, Reiter's syndrome, sarcoidosis, scleroderma, spondyloarthropathies, Still's disease, stroke, therapy associated syndrome, therapy induced inflammatory syndrome, inflammatory syndrome following IL-2 administration, thoracoabdominal aortic aneurysm repair (TAAA), Vasulo-Behcet's disease, Yellow Fever vaccination, type 1 diabetes mellitus, type 2 diabetes mellitus, neuropathic pain, sciatica, cerebral edema, edema in and/or around the spinal cord, vasculitide, Wegener's granulomatosis, temporal arteritis, polymyalgia rheumatica, Takayasu's arteritis, polyarteritis nodosa, microscopic polyangiitis, Churg-Strauss syndrome, Felty's syndrome, Sjogren's syndrome, mixed connective tissue disorder, relapsing polychondritis, pseudogout, loosening of prostheses, autoimmune hepatitis, sclerosing cholangitis, acute pancreatitis, chronic pancreatitis, glomerulonephritides, post-streptococcal glomerulonephritis or IgA nephropathy, rheumatic heart disease, cardiomyopathy, orchitis, pyoderma gangerenosum, multiple myeloma, TNF receptor associated periodic syndrome [TRAPS], atherosclerosis, steroid dependent giant cell arteritismyostitis, uveitis, and drug reactions.

The invention is further illustrated in the following examples, which should not be construed as further limiting. The contents of all references, pending patent applications and published patents, cited throughout this application are hereby expressly incorporated by reference.

EXAMPLES

Example 1: Preparation of the Formulation

The pharmaceutical formulation of the invention was made according to the following protocol.

Materials which were used in the formulation include: mannitol, citric acid monohydrate (citric acid), sodium citrate, disodium phosphate dihydrate (dibasic sodium phosphate dihydrate), sodium dihydrogen phosphate dihydrate (monobasic sodium phosphate dihydrate), sodium chloride, polysorbate 80, water for the injections, sodium hydroxide, which was used as a 1M solution to adjust the pH, and protein concentrate (e.g., antibody concentrate).

Preparation of 20 L of Buffer (Equivalent to 20.180 kg—Density of the Solution: 1.009 g/ml)

Ingredients were weighed out as follows: 240.0 g mannitol, 26.1 g citric acid monohydrate, 6.1 g sodium citrate, 30.6 g disodium phosphate dihydrate, 17.2 g sodium dihydrogen phosphate dihydrate, 123.3 g sodium chloride, 20.0 g polysorbate 80, and 19,715.7 to 19,716.1 g of water.

A sodium hydroxide solution was prepared by combining 40.0 g of sodium hydroxide with 1000.8 g of water for injections.

Next, a buffer was prepared by dissolving the following pre-weighed ingredients (described above) in about 90% of the water for injections: mannitol, citric acid monohydrate, sodium citrate, disodium phosphate dihydrate, sodium dihydrogen phosphate, sodium chloride, and polysorbate 80. It was determined that the sequence of the addition of the buffer constituents was not important and can, therefore, be chosen at will.

Following addition of all of the buffer constituents, the pH of the solution was adjusted with 1M sodium hydroxide which was prepared as described above. After the addition of the sodium hydroxide, the final weight of the water was added. The buffer solution was then filtered through a sterilized filter (hydrophilic polyvinylidene difluoride, 0.22 µm pore size) into a sterilized receptacle. The filtration medium used was filtration sterilized nitrogen.

Preparation of 40 L of Formulation (Equivalent to 40.88 kg)

The filtered buffer solution was then added to the thawed and pooled antibody concentrate (the active ingredient of the pharmaceutical formulation), prepared as follows. The antibody (concentrate) was thawed in a water bath prior to the preparation of the pharmaceutical formulation. 34.207 g of antibody concentrate was used, which is equivalent to 2.0 kg of protein with 60 mg protein/mL protein concentrate. The density of the concentrate was 1.0262 g/mL. Any protein concentrate ranging from 25.655 to 37.316, which is equivalent to a protein concentration in the protein concentrate of 55 to 80 mg/mL, can be used. The buffer was added while stirring, until the final weight of the bulk solution was reached.

properties of the D2E7 antibody drug substance as evidenced by the lower number of subvisible particles regardless whether a slow or fast freeze/thaw cycle was being used (see table 2).

TABLE 2

Effect of freeze thaw on the D2E7 antibody drug substance with/without polysorbate 80

| Test criteria | Polysorbate (0.1%)[1)] | No freeze/ thaw | Slow thaw −30° C. in refrigerator | Fast thaw −30° C. in water bath | Slow thaw −80° in refrigerator | Fast thaw −80° C. in water bath |
|---|---|---|---|---|---|---|
| Clarity | − | 25.0 | 22.5 | 25.3 | 25.8 | 25.6 |
|  | + | 27.8 | 28.1 | 28.2 | 28.0 | 28.1 |
| Colour | − | ≤B9 | ≤B9 | ≤B9 | ≤B9 | ≤B9 |
|  | + | ≤B9 | ≤B9 | ≤B9 | ≤B9 | ≤B9 |
| pH | − | 5.01 | 5.02 | 5.02 | 5.02 | 5.02 |
|  | + | 5.02 | 5.02 | 5.02 | 5.02 | 5.02 |
| Subvisible particles | − | 42 | 600 | 303 | 1891 | 303 |
|  |  | 2 | 4 | 5 | 8 | 0 |
|  | + | 0 | 5 | 1 | 0 | 8 |
|  |  | 0 | 0 | 0 | 0 | 1 |
| Size exclusion HPLC | − | 99.8 | 99.8 | 99.8 | 99.8 | 99.8 |
|  | + | 99.8 | 99.8 | 99.8 | 99.8 | 99.8 |
| Cation exchange HPLC | − | 87.1 | 87.0 | 87.2 | 86.9 | 86.9 |
|  | + | 86.8 | 87.0 | 87.1 | 87.3 | 86.8 |
| In vitro TNF neutralization test | − | 118.0 | 123.8 | 118.0 | 103.3 | 120.5 |
|  | + | 111.8 | 96.2 | 100.9 | 96.7 | 95.8 |

[1)]+ = formulation with 0.1% polysorbate 80; − = formulation without 0.1% polysorbate 80

The formulation, with all of its ingredients included, was then sterilized by filtration as described above, except the formulation was filtered through two sterile 0.22 μm membrane filters. Following sterilization, the formulation was packaged for use in either a vial or a pre-filled syringe.

The skilled artisan will also appreciate that the weight quantities and/or weight-to-volume ratios recited herein, can be converted to moles and/or molarities using the art-recognized molecular weights of the recited ingredients. Weight quantities exemplified herein (e.g., g or kg) are for the volumes (e.g., of buffer or pharmaceutical formulation) recited. The skilled artisan will appreciate that the weight quantities can be proportionally adjusted when different formulation volumes are desired. For example, 32 L, 20 L, 10 L, 5 L, or 1 L formulations would include 80%, 50%, 25%, 12.5%, or 2.5%, respectively, of the exemplified weight quantities.

Example 2: Freeze/Thaw Studies

After the formulation buffer for the D2E7 antibody was selected the drug substance was formulated in the same matrix as the finished product.

Freeze thaw behavior of the D2E7 antibody drug substance at a protein concentration of 63 mg/mL was evaluated by cycling drug substance 3 times from the frozen state to the liquid state. Table N shows the results of an experiment evaluating the effect of three fast and slow freeze-thaw cycles in the presence and absence of 0.1% polysorbate 80 starting from −80° C. or −30° C., respectively.

Table 2 shows that the D2E7 antibody drug substance can be thawed/frozen at least 3 times without any detrimental effect on either chemical (cation exchange HPLC, size exclusion HPLC, colour, pH), physicochemical properties (subvisible particles, clarity) or biological activity (in vitro TNF neutralization assay). Also table 2 shows that the inclusion of polysorbate 80 improved the physicochemical Example 3: Microbial Studies Tests were performed to determine if the formulation can support microbial growth. The results from these experiments showed that the formulation does not support microbial growth if stored at 20 to 25° C. for 14 days. This result was determined by directly inoculating the sterile formulation with microorganisms (e.g., *Staphylococous aureus*, ATCC-No.: 6538P, *Candida albicans*, ATCC-No.: 10231, *Aspergillus niger*, ATCCC-No.: 16404, *Pseudomonas aeruginosa*, ATCC-No.: 9027, an environmental isolate) at low level (NMT 100 cfu/mL). Inoculated formulations were then examined for overall microbial growth, e.g., for changes in turbidity. A lack of turbidity was an indication of no overall growth, and was detected in the inoculated containers after 14 days. Further, no organisms could be reisolated from these containers. Thus it was concluded that the formulation does not support microbial growth under these conditions.

INCORPORATION BY REFERENCE

The contents of all references and patents cited herein are hereby incorporated by reference in their entirety.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A stable liquid aqueous pharmaceutical formulation comprising
   (a) a human IgG1 anti-human Tumor Necrosis Factor alpha (TNFα) antibody at a concentration of 50 mg/ml,
   (b) a polyol,
   (c) a polysorbate, and
   (d) a buffer system comprising citrate and phosphate and having a pH of 4 to 8,
   wherein the antibody is D2E7, and
   wherein the formulation is suitable for subcutaneous injection.

2. The formulation of claim 1, wherein the polysorbate is polysorbate 20 or polysorbate 80.

3. The formulation of claim 2, wherein the polysorbate is polysorbate 80.

4. The formulation of claim 3, wherein the polysorbate 80 concentration is between 0.1 and 10 mg/ml.

5. The formulation of claim 1, wherein the pH is from 4.5 to 6.0.

6. The formulation of claim 1, wherein the pH is from 4.8 to 5.5.

7. The formulation of claim 1, wherein the polyol is a sugar alcohol.

8. The formulation of claim 7, wherein the sugar alcohol is mannitol.

9. The formulation of claim 7, wherein the sugar alcohol is sorbitol.

10. The formulation of claim 7, wherein the polysorbate is polysorbate 20 or polysorbate 80.

11. The formulation of claim 10, wherein the polysorbate is polysorbate 80.

12. The formulation of claim 10, wherein the pH is from 4.5 to 6.0.

13. The formulation of claim 10, wherein the pH is from 4.8 to 5.5.

14. The formulation of claim 1, wherein the polyol is a sugar.

15. The formulation of claim 14, wherein the sugar is a non-reducing sugar.

16. The formulation of claim 14, wherein the sugar is trehalose or sucrose.

17. The formulation of claim 14, wherein the polysorbate is polysorbate 20 or polysorbate 80.

18. The formulation of claim 17, wherein the polysorbate is polysorbate 80.

19. The formulation of claim 17, wherein the pH is from 4.5 to 6.0.

20. The formulation of claim 17, wherein the pH is from 4.8 to 5.5.

* * * * *

SEQUENCE LISTING

<160> NUMBER OF SEQ ID NOS: 34

<210> SEQ ID NO 1
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutated human antibody

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105

<210> SEQ ID NO 2
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutated human antibody

<400> SEQUENCE: 2

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120

<210> SEQ ID NO 3
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<223> OTHER INFORMATION: Mutated human antibody
<220> FEATURE:
<221> NAME/KEY: MOD_RES
<222> LOCATION: (9)..(9)
<223> OTHER INFORMATION: Thr or Ala

<400> SEQUENCE: 3

Gln Arg Tyr Asn Arg Ala Pro Tyr Xaa
1               5

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Mutated human antibody
<220> FEATURE:
<221> NAME/KEY: MOD_RES
<222> LOCATION: (12)..(12)
<223> OTHER INFORMATION: Tyr or Asn

<400> SEQUENCE: 4

Val Ser Tyr Leu Ser Thr Ala Ser Ser Leu Asp Xaa
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Mutated human antibody

<400> SEQUENCE: 5

Ala Ala Ser Thr Leu Gln Ser
1               5

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Mutated human antibody

<400> SEQUENCE: 6

Ala Ile Thr Trp Asn Ser Gly His Ile Asp Tyr Ala Asp Ser Val Glu
1               5                   10                  15

Gly

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Mutated human antibody
```

```
<400> SEQUENCE: 7

Arg Ala Ser Gln Gly Ile Arg Asn Tyr Leu Ala
1               5                   10

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Mutated human antibody

<400> SEQUENCE: 8

Asp Tyr Ala Met His
1               5

<210> SEQ ID NO 9

<400> SEQUENCE: 9

000

<210> SEQ ID NO 10

<400> SEQUENCE: 10

000

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Mutated human antibody

<400> SEQUENCE: 11

Gln Lys Tyr Asn Ser Ala Pro Tyr Ala
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Mutated human antibody

<400> SEQUENCE: 12

Gln Lys Tyr Asn Arg Ala Pro Tyr Ala
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Mutated human antibody
```

```
<400> SEQUENCE: 13

Gln Lys Tyr Gln Arg Ala Pro Tyr Thr
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Mutated human antibody

<400> SEQUENCE: 14

Gln Lys Tyr Ser Ser Ala Pro Tyr Thr
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Mutated human antibody

<400> SEQUENCE: 15

Gln Lys Tyr Asn Ser Ala Pro Tyr Thr
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Mutated human antibody

<400> SEQUENCE: 16

Gln Lys Tyr Asn Arg Ala Pro Tyr Thr
1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Mutated human antibody

<400> SEQUENCE: 17

Gln Lys Tyr Asn Ser Ala Pro Tyr Tyr
1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Mutated human antibody
```

```
<400> SEQUENCE: 18

Gln Lys Tyr Asn Ser Ala Pro Tyr Asn
1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Mutated human antibody

<400> SEQUENCE: 19

Gln Lys Tyr Thr Ser Ala Pro Tyr Thr
1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Mutated human antibody

<400> SEQUENCE: 20

Gln Lys Tyr Asn Arg Ala Pro Tyr Asn
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Mutated human antibody

<400> SEQUENCE: 21

Gln Lys Tyr Asn Ser Ala Ala Tyr Ser
1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Mutated human antibody

<400> SEQUENCE: 22

Gln Gln Tyr Asn Ser Ala Pro Asp Thr
1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Mutated human antibody
```

```
<400> SEQUENCE: 23

Gln Lys Tyr Asn Ser Asp Pro Tyr Thr
1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Mutated human antibody

<400> SEQUENCE: 24

Gln Lys Tyr Ile Ser Ala Pro Tyr Thr
1               5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Mutated human antibody

<400> SEQUENCE: 25

Gln Lys Tyr Asn Arg Pro Pro Tyr Thr
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Mutated human antibody

<400> SEQUENCE: 26

Gln Arg Tyr Asn Arg Ala Pro Tyr Ala
1               5

<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Mutated human antibody

<400> SEQUENCE: 27

Ala Ser Tyr Leu Ser Thr Ser Ser Ser Leu Asp Asn
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Mutated human antibody
```

```
<400> SEQUENCE: 28

Ala Ser Tyr Leu Ser Thr Ser Ser Ser Leu Asp Lys
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Mutated human antibody

<400> SEQUENCE: 29

Ala Ser Tyr Leu Ser Thr Ser Ser Ser Leu Asp Tyr
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Mutated human antibody

<400> SEQUENCE: 30

Ala Ser Tyr Leu Ser Thr Ser Ser Ser Leu Asp Asp
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Mutated human antibody

<400> SEQUENCE: 31

Ala Ser Tyr Leu Ser Thr Ser Phe Ser Leu Asp Tyr
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Mutated human antibody

<400> SEQUENCE: 32

Ala Ser Tyr Leu Ser Thr Ser Ser Ser Leu His Tyr
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Mutated human antibody
```

```
<400> SEQUENCE: 33

Ala Ser Phe Leu Ser Thr Ser Ser Ser Leu Glu Tyr
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Mutated human antibody

<400> SEQUENCE: 34

Ala Ser Tyr Leu Ser Thr Ala Ser Ser Leu Glu Tyr
1               5                   10
```